(12) United States Patent
Cassidy et al.

(10) Patent No.: US 6,480,257 B2
(45) Date of Patent: Nov. 12, 2002

(54) HEAT EXCHANGER USEABLE IN WEARABLE FLUID HEATER

(75) Inventors: David Cassidy, Chelmsford, MA (US); Russell Hart, North Attleboro, MA (US); John Landy, Billerica, MA (US); Andrea Stamp, Gloucester, MA (US)

(73) Assignee: Belmont Instrument Corporation, Billerica, MA (US)

( * ) Notice: Subject to any disclaimer, the term of this patent is extended or adjusted under 35 U.S.C. 154(b) by 31 days.

(21) Appl. No.: 09/734,108

(22) Filed: Dec. 11, 2000

(65) Prior Publication Data

US 2001/0011585 A1 Aug. 9, 2001

Related U.S. Application Data

(63) Continuation-in-part of application No. 09/113,255, filed on Jul. 10, 1998, now Pat. No. 6,175,688.

(51) Int. Cl.[7] .................................................. A61F 7/60
(52) U.S. Cl. ......................... 352/470; 604/113; 165/46
(58) Field of Search ................ 392/470, 478, 392/465, 475; 604/113, 114, 93; 165/46

(56) References Cited

U.S. PATENT DOCUMENTS

| 3,399,536 A | 9/1968 | Walz |
| 3,443,060 A | 5/1969 | Smith |
| 3,475,590 A | 10/1969 | Pins |
| 3,485,245 A | 12/1969 | Lahr et al. |
| 3,590,215 A | 6/1971 | Anderson et al. |
| 3,614,385 A | 10/1971 | Horstmann |
| 3,640,283 A | 2/1972 | Bhatia et al. |
| 3,853,479 A | 12/1974 | Talonn et al. |
| 4,038,519 A | 7/1977 | Foucras |
| 4,108,146 A | 8/1978 | Golden |
| 4,167,663 A | 9/1979 | Granzow, Jr. et al. |
| 4,293,762 A | 10/1981 | Ogawa |
| 4,309,592 A | 1/1982 | Le Boeuf |

(List continued on next page.)

FOREIGN PATENT DOCUMENTS

| DE | 93 18 886 U | 3/1994 |
| WO | WO92/17040 | 10/1992 |
| WO | WO96/40331 | 12/1996 |

OTHER PUBLICATIONS

PCT Invitation To Pay Additional Fees for International Application No. PCT/US99/13627, International Filing Date Jun. 16, 1999.
PCT Notification of Transmittal of the International Search Report of Serial No. PCT/US9913627, Nov. 8, 1999.
International Search Report of Serial No. PCT/US99/13627, Nov. 8, 1999.

*Primary Examiner*—Teresa Walberg
*Assistant Examiner*—Thor S. Campbell
(74) *Attorney, Agent, or Firm*—Cesari and McKenna, LLP

(57) ABSTRACT

A heat exchanger that is useable in a wearable fluid heater is disclosed. Mechanisms may be used with or comprised in embodiments of the heat exchanger for purging gas from the heat exchanger.

27 Claims, 27 Drawing Sheets

U.S. PATENT DOCUMENTS

| | | |
|---|---|---|
| 4,314,143 A | 2/1982 | Bilstad et al. |
| 4,356,383 A | 10/1982 | Dahlberg et al. |
| 4,384,578 A | 5/1983 | Winkler |
| 4,464,563 A | 8/1984 | Jewett |
| 4,532,414 A | 7/1985 | Shah et al. |
| 4,574,876 A | 3/1986 | Aid |
| 4,678,460 A | 7/1987 | Rosner |
| 4,680,445 A | 7/1987 | Ogawa |
| 4,707,587 A | 11/1987 | Greenblatt |
| 4,731,072 A | 3/1988 | Aid |
| 4,759,749 A | 7/1988 | Verkaart |
| 4,782,212 A | 11/1988 | Bakke |
| 4,801,777 A | 1/1989 | Auberach |
| 4,844,074 A | 7/1989 | Kurucz |
| 4,847,470 A | 7/1989 | Bakke |
| 4,878,537 A | 11/1989 | Verkaart |
| 4,906,816 A | 3/1990 | van Leerdam |
| 4,908,014 A | 3/1990 | Kroyer |
| 4,938,279 A | 7/1990 | Betker |
| 4,962,761 A | 10/1990 | Golden |
| 5,062,775 A | 11/1991 | Orth |
| 5,108,372 A | 4/1992 | Swenson |
| 5,125,069 A | 6/1992 | O'Boyle |
| 5,188,604 A | 2/1993 | Orth |
| 5,245,693 A | 9/1993 | Ford et al. |
| 5,250,032 A | 10/1993 | Carter, Jr. et al. |
| 5,254,094 A | 10/1993 | Starkey et al. |
| 5,344,568 A | 9/1994 | Kitaevich et al. |
| 5,381,510 A | 1/1995 | Ford et al. |
| 5,408,577 A | 4/1995 | Weber, Jr. et al. |
| 5,420,962 A * | 5/1995 | Bakke ................. 392/379 |
| 5,690,815 A | 11/1997 | Krasnoff et al. |
| 5,702,358 A | 12/1997 | Witherspoon et al. |
| 5,846,224 A | 12/1998 | Saword et al. |
| 6,045,648 A * | 4/2000 | Palmgren et al. ........ 156/272.4 |

* cited by examiner

HEAT EXCHANGER USEABLE IN WEARABLE FLUID HEATER

CROSS-REFERENCE TO RELATED APPLICATION

This application is a continuation-in-part of copending U.S. patent application Ser. No. 09/113,255 filed Jul. 10, 1998, now U.S. Pat. No. 6,175,688 entitled "Wearable Intravenous Fluid Heater." The entirety of said copending application is hereby incorporated herein by reference.

BACKGROUND OF THE INVENTION

1. Field of the Invention

The present invention relates generally to a heat exchanger that may be used in a device for heating to a desired infusion temperature a fluid to be infused to a patient. Although the present invention finds particular utility in heating of fluids which are to be supplied intravenously at relatively low flow rates (e.g., below about 2550 ml/hour for fluids to be heated to an infusion temperature of between 38–42 degrees C. from an input temperature into the device of 10 degrees C., or below about 3600 ml/hour for fluids to be heated to such an infusion temperature from an input temperature of 18 degrees C.), it should be understood that other utilities are also contemplated for the present invention (e.g., including in connection with infusion of other types of fluids at other temperatures and flow rates, and infusion of fluids in ways other than by intravenous infusion).

2. Brief Description of Related Prior Art

Many prior art techniques and devices exist for warming fluids to be infused intravenously into humans and other animals. One such conventional device is disclosed in U.S. Pat. No. 5,245,693 ("the '693 patent"). The '693 patent is directed to an intravenous fluid heater that includes a disposable cassette containing a heat exchanger. The preferred embodiment of the heat exchanger disclosed in the '693 patent includes a passageway-defining inner layer sandwiched between a pair of flexible, metal foil membranes. The inner layer defines an extended, e.g., serpentine, path for fluid to be warmed, and serves to space apart and insulate the metal foil membranes from one another. Inlet and outlet ports to the serpentine fluid path are defined in one of the two foil membranes. Heat generated by heating elements which sandwich the heat exchanger is transferred through the metal foil membranes to the fluid flowing through the serpentine path. The heating elements are designed to be graduated, that is, to generate more heat in the area of the inlet portion of the serpentine path than in the area of its outlet.

Unfortunately, the heating device disclosed in the '693 patent suffers from several disadvantages. First, the heating device disclosed in the '693 patent is not wearable by the patient adjacent the fluid infusion situs. This means that the length of tubing required to deliver the heated fluid from the device to the infusion situs may vary depending upon where the device is positioned relative to the patient, but will always be longer than that which would be required if the device were being worn by the patient at or near the infusion situs. This means that in the infusion arrangement disclosed in the '693 patent, the temperature of the heated fluid exiting the heating device will always drop, prior to being infused into the patient, more than would be the case if the heating device were wearable adjacent the infusion situs. The temperature drop of the heated fluid can be especially pronounced at the aforesaid relatively low fluid flow rates. Unfortunately, a significant proportion of intravenous fluid infusions take place at such low flow rates.

A yet further disadvantage of the '693 patent's heating arrangement is that although means are included reducing gas bubble formation in the infusion fluid, such means may not always be sufficient when used alone to adequately reduce or eliminate such bubbles prior to infusion of the fluid into the patient. As will be appreciated by those skilled in the art, if left unchecked, this type of condition can be, at minimum, deleterious to patient well-being, and at most, life-threatening.

Another conventional infusion fluid warming device is disclosed in U.S. Pat. No. 5,254,094 ("the '094 patent"). In the arrangement disclosed in the '094 patent, a box which may be attached to a patient's arm is provided. Two chambers are included in the box, containing a heat exchanger element constructed from a continuous length of stainless steel tubing in the form of two parallel coils which are connected to each other by a straight length of tubing. The box includes a passage between the chambers such that a warming fluid may be introduced through an aperture in the box into one of the chambers, flow into the other chamber, and then exit the warmer through another aperture in the box. The infusion fluid to be warmed is supplied to the coils through a first flexible plastic inlet tube and discharged for infusion into a patient through a second flexible plastic tube. The warming fluid is supplied via fluid supply tubing to the box from a separate fluid source that is not dimensioned or suitable for being worn by the patient, such as a water heater. A temperature sensor located in the infusion fluid path between the box and the infusion situs may be provided for generating signals indicative of the temperature of the infusion fluid for provision to a microprocessor contained in the same unit comprising the water heater. The microprocessor also receives outputs from a water temperature sensor and controls the water heater, based upon the outputs from these sensors and a desired infusion fluid temperature set by the user, so as to maintain the heating water at a temperature for heating the infusion fluid to the desired temperature.

Disadvantageously, use of a warming fluid/infusion fluid type of heat exchanger, and a warming fluid heater that is remote from the heat exchanger and not wearable by the patient, make '094 patent's arrangement bulky, and relatively difficult to move and set up for use. Also disadvantageously, as is the case in the '693 patent, the '094 patent fails to disclose sufficient means for reducing gas bubbles in infusion fluid prior to infusion of the fluid into the patient.

Other examples of infusion fluid warming prior art are disclosed in U.S. Pat. Nos. 5,381,510, 4,731,072, 3,443,060, 3,475,590, 3,485,245, 3,590,215, 3,614,385, 3,640,283, 3,853,479, 4,038,519, 4,108,146, 4,167,663, 4,293,762, 4,309,592, 4,938,279, 4,847,470, 4,574,876, 3,399,536, 4,962,761, 5,125,069, 4,908,014, 4,906,816, 4,844,074, 4,707,587, 4,759,749, 4,782,212, 4,801,777, 4,680,445, 4,678,460, 4,532,414, 4,464,563, 4,314,143, 4,356,383, and 4,878,537. Unfortunately, the prior art disclosed in each of these patents suffers from the aforesaid and/or other disadvantages and drawbacks.

SUMMARY OF THE INVENTION

In accordance with the present invention, a heat exchanger is provided that may be used in an intravenous fluid heater that is dimensioned to be wearable adjacent a patient's intravenous fluid infusion situs. In one embodiment of the present invention, the heat exchanger includes two flexible walls that contact respective heating elements of the fluid heater when the heat exchanger is used in the heater.

The heat exchanger also includes at least one member that is inserted between the flexible walls, and together with the flexible walls, defines a flow path for fluid through the heater when the heat exchanger is used in the heater. Alternatively, the at least one member may be eliminated, and the two walls may be spot welded together at selected locations along the walls in such a way as to define the flow path. When the heat exchanger is used in the heater, the heat exchanger is physically unattached to the heater and is removable from the heater (e.g., after being used in the heater).

The heater and heat exchanger may be dimensioned to be wearable by a patient adjacent a fluid infusion situs of the patient. In this embodiment, the flexible walls and member may be made of plastic (e.g., respective polyester plastic films coated with respective outer coatings of acrylic), and the flexible walls may be bonded to the member.

The fluid flow path through the heater may include a fluid inlet, fluid outlet, and serpentine channel between the inlet and outlet. The flexible walls may be identically-dimensioned sheets that contact respective internal sides of flared portions of the member, and completely cover, from opposite respective sides of the member, the channel.

When the heat exchanger is in use in the heater, the heater is in sealing engagement with the heat exchanger, such that an air and liquid tight seal is formed between the heat exchanger and the heater.

In another embodiment of the present invention, at least one of the flexible walls is porous and hydrophobic, and the number and size of the pores in the wall permit gas to be vented from the fluid in the exchanger through the pores, but prevent flow of liquid and bacteria therethrough. In this alternative embodiment, the other flexible wall may be made of polycarbonate and may be thinner than the porous hydrophobic wall of the exchanger. The porous wall may be made of an expanded polytetrafluoro-ethylene material.

In yet another embodiment of the present invention, the heat exchanger may include first and second fluid outlets, and one fluid inlet. The heat exchanger may be constructed such that when the heat exchanger is impinged upon by a pressurizing and gas purging mechanism, the inlet and the first outlet may become occluded, and fluid and gas in the flow path defined by the heat exchanger may be forced (by pressure forces applied to the heat exchanger by the mechanism) through the second outlet, and thence, out of the heat exchanger.

The pressurizing mechanism may comprise a cam system that may apply both a first force and a second force to the heat exchanger. The first force may cause the inlet and the first outlet of the heat exchanger to become occluded. The second force may cause the fluid and the gas to be forced out of the heat exchanger via the second outlet.

The cam mechanism may comprise a plurality of cams. Each of the cams may be actuated by a respective force applied to the cam by a respective change in length and/or shape of a respective wire or filament made of shape-memory alloy. The wire may undergo such change in length and/or shape when heated (e.g., as a result of application of electricity thereto) to apply the force to the cam. The heat exchanger may be disposed in an external housing, and the cam may be positioned between the housing and the heat exchanger.

The heat exchanger may also include or be connected to a hydrophobic membrane that vents the gas to the ambient environment. The hydrophobic membrane may be in fluid communication with the inlet. A check valve may be employed to prevent return fluid flow into the heat exchanger via the second outlet.

Thus, the heat exchanger of the present invention, when used in the heater, is physical unattached to the heater and is removable from the heater when not in use in the heater. Advantageously, this permits the heat exchanger to be disposable/replaceable, and the remainder of the heater to be reusable.

Also in accordance with the present invention, the entire fluid heating assembly (i.e., including the heat exchanger and heater) may be dimensioned so as to be wearable adjacent the patient's fluid infusion situs. Additionally, when at least one wall of the heat exchanger is porous and gas permeable, or the heat exchanger is constructed for use with the aforedescribed pressurizing and gas purging mechanism, dissolved gas (e.g., air) in the fluid in the heat exchanger may be vented or purged to the ambient environment prior to infusion of the fluid into the patient. Advantageously, these features provided in accordance with the present invention permit a fluid heater assembly using a heat exchanger in accordance with the present invention to overcome the aforesaid and other disadvantages of the '693 and '094 patents.

Other features and advantages of the present invention will become apparent as the following Detailed Description proceeds and upon reference to the Drawings, wherein like numerals depict like parts, and in which:

BRIEF DESCRIPTION OF THE DRAWINGS

FIG. 3 is a perspective view of the portion of the disposable heat exchanger of

FIG. 2 that defines a serpentine flow path for the infusion fluid.

Figure 1:
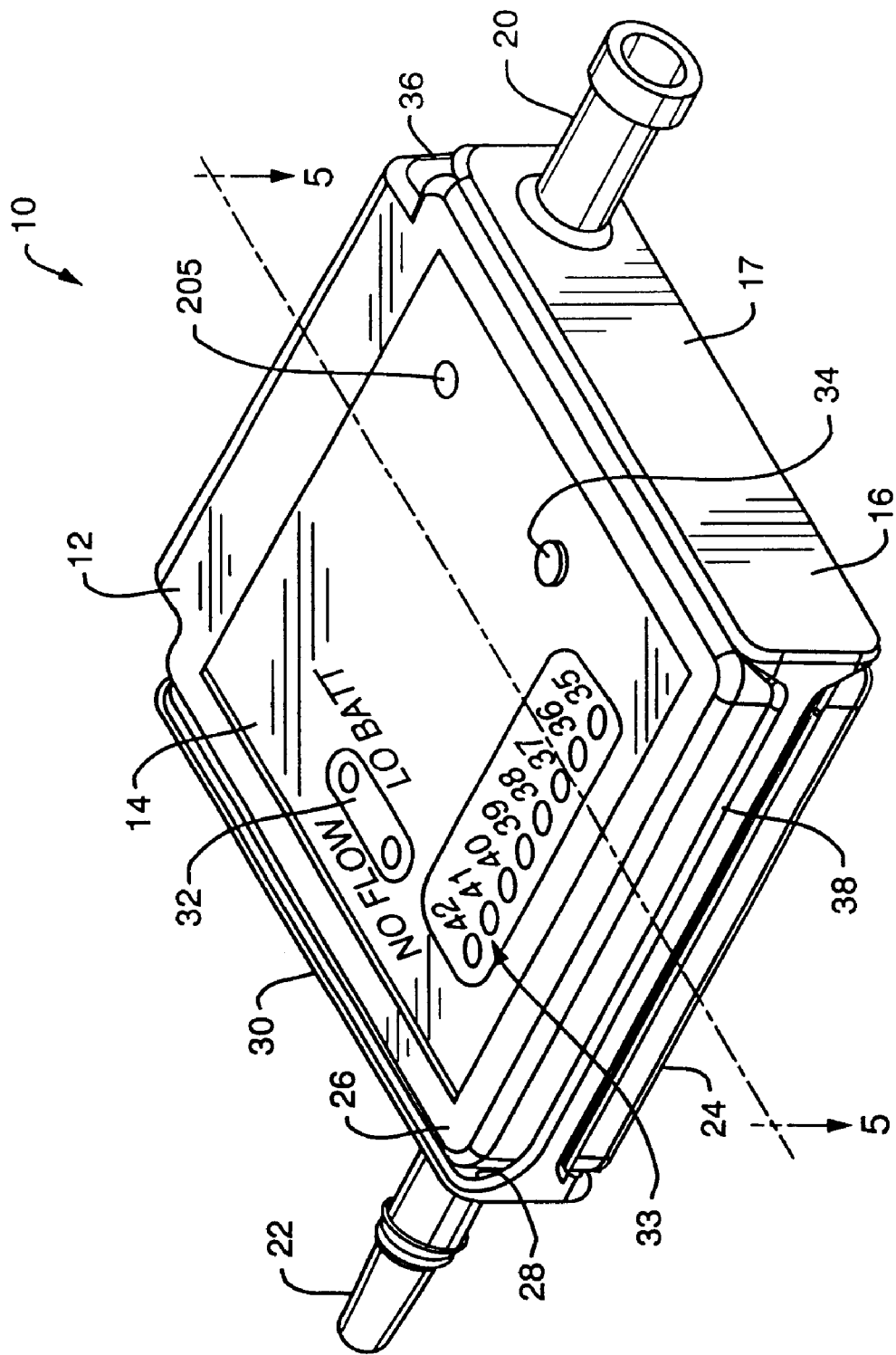
FIG. 1 is an outside perspective view of an intravenous fluid heater in which the heat exchanger of the present invention may be used, and also wherein the strap mechanism for fastening the heater to the patient has been removed for purposes of clarity of illustration.
Figure 2:
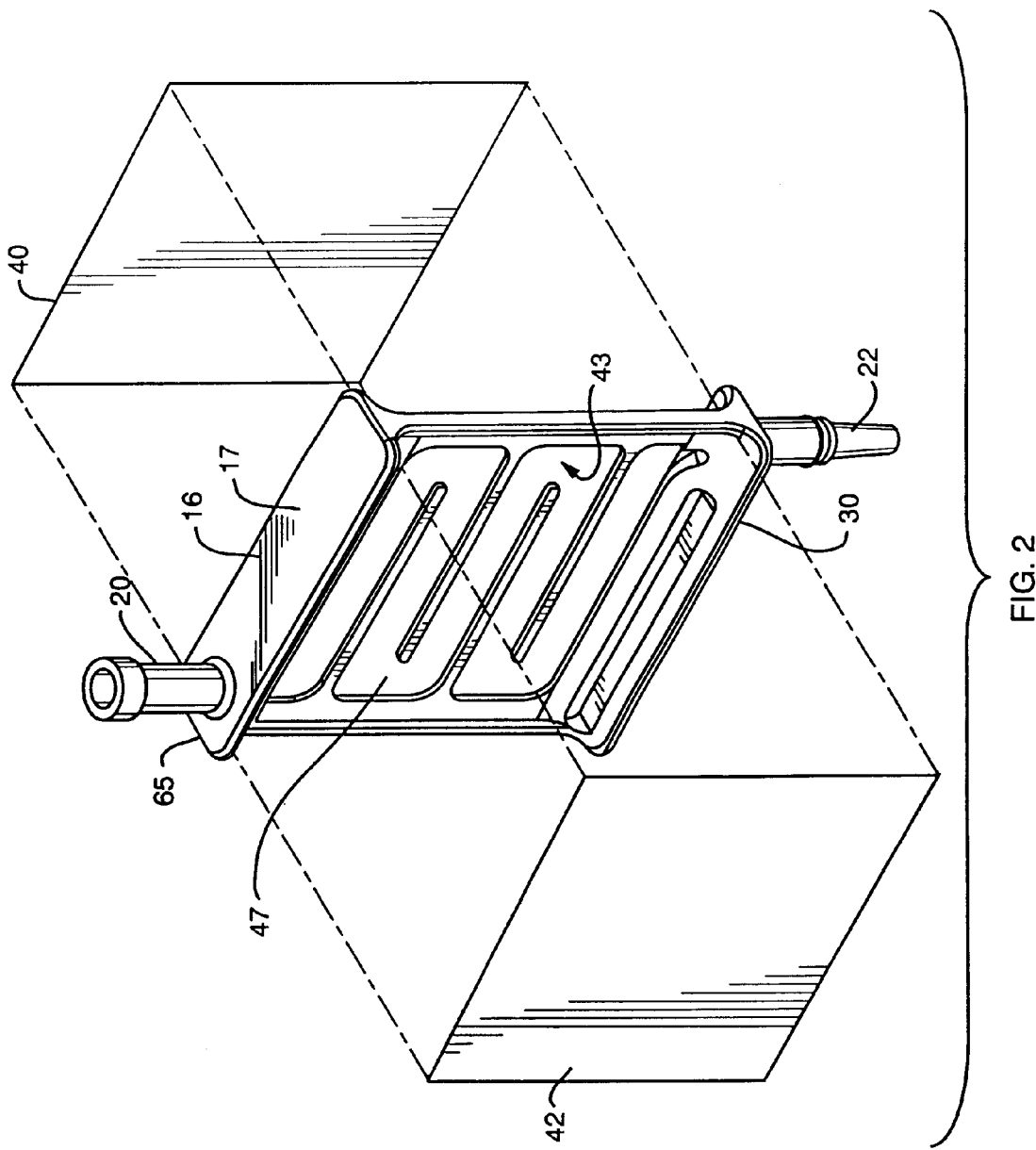
FIG. 2 is an exploded perspective view of one embodiment of the heat exchanger of the present invention.
Figure 3:
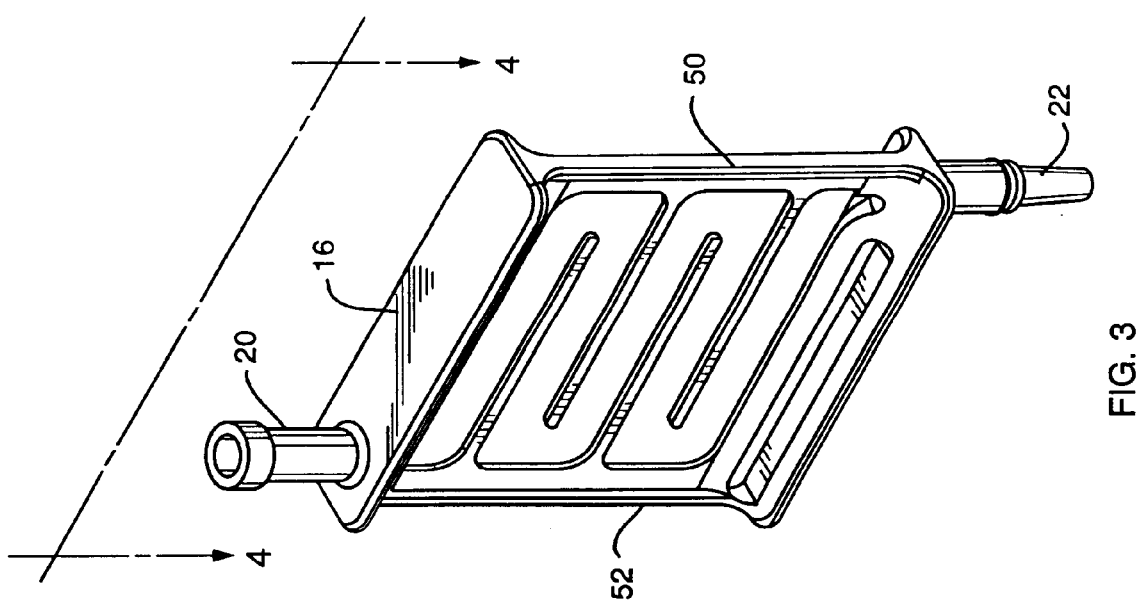
Figure 4:
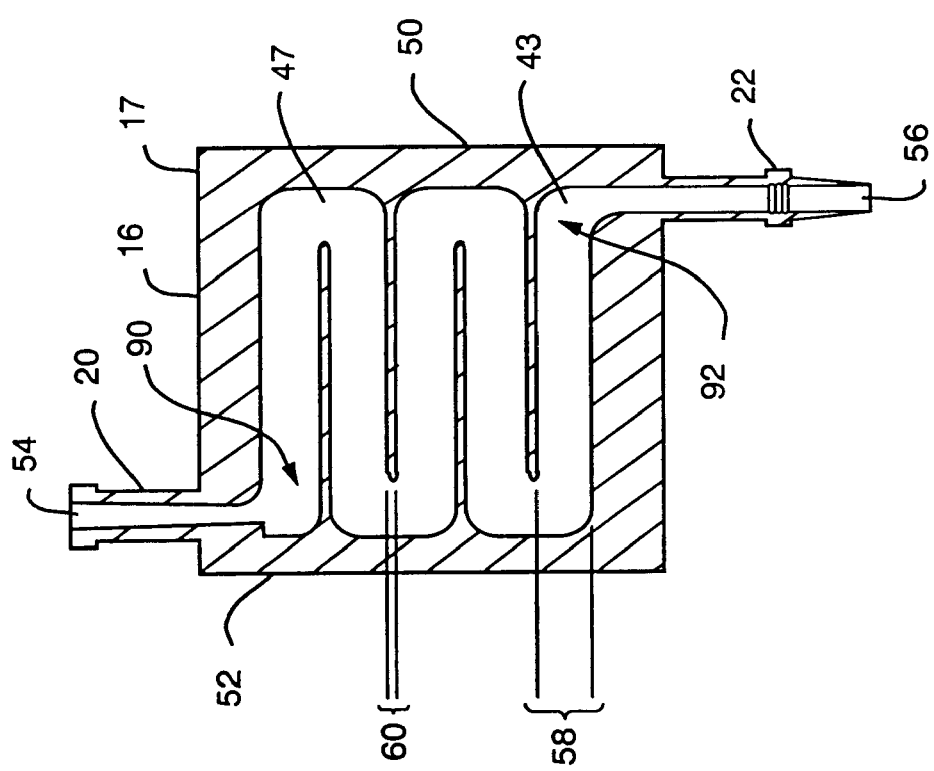
FIG. 4 is a cross-sectional view taken along lines 4—4 of FIG. 3.
Figure 5:
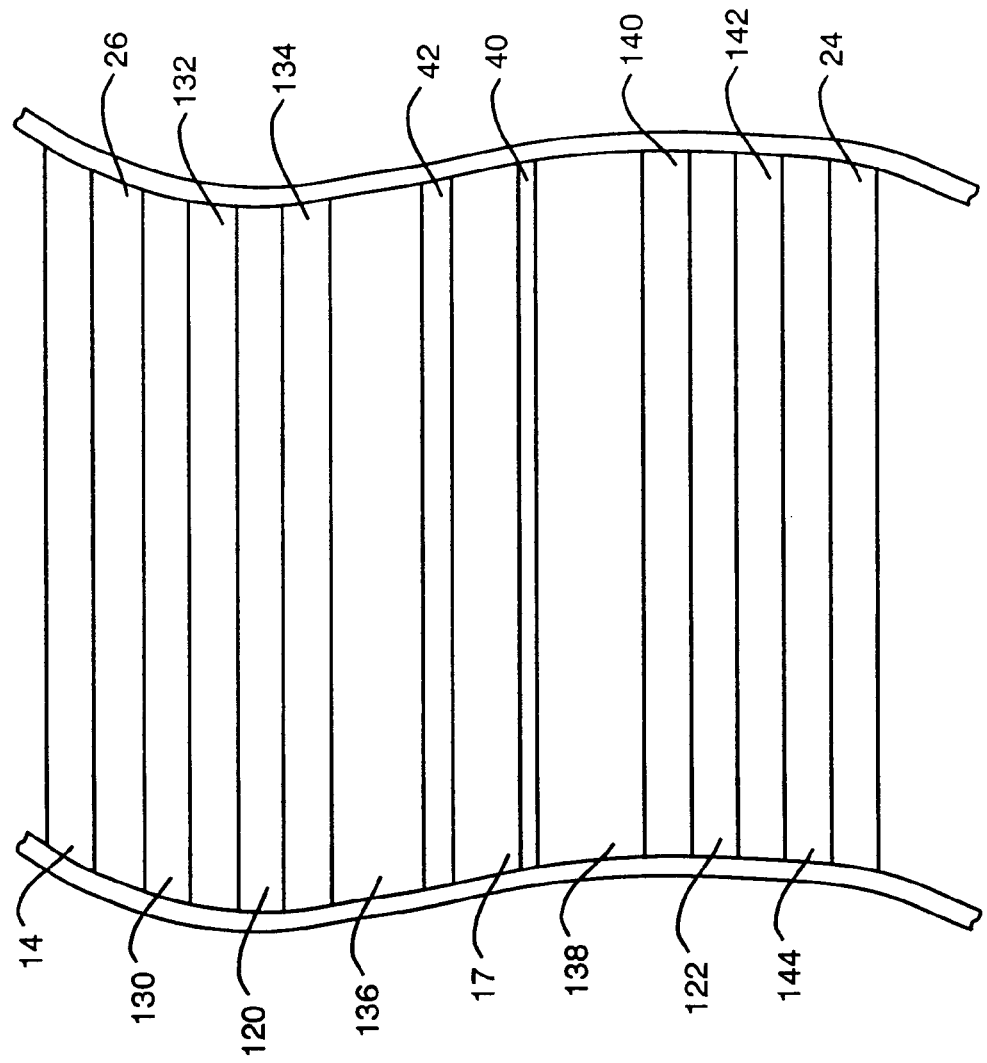
FIG. 5 is a highly schematic, partial cross-sectional view taken along lines 5—5 of FIG. 1 for illustrating, in a general fashion, the layered construction of the heater shown in FIG. 1.
Figure 6:
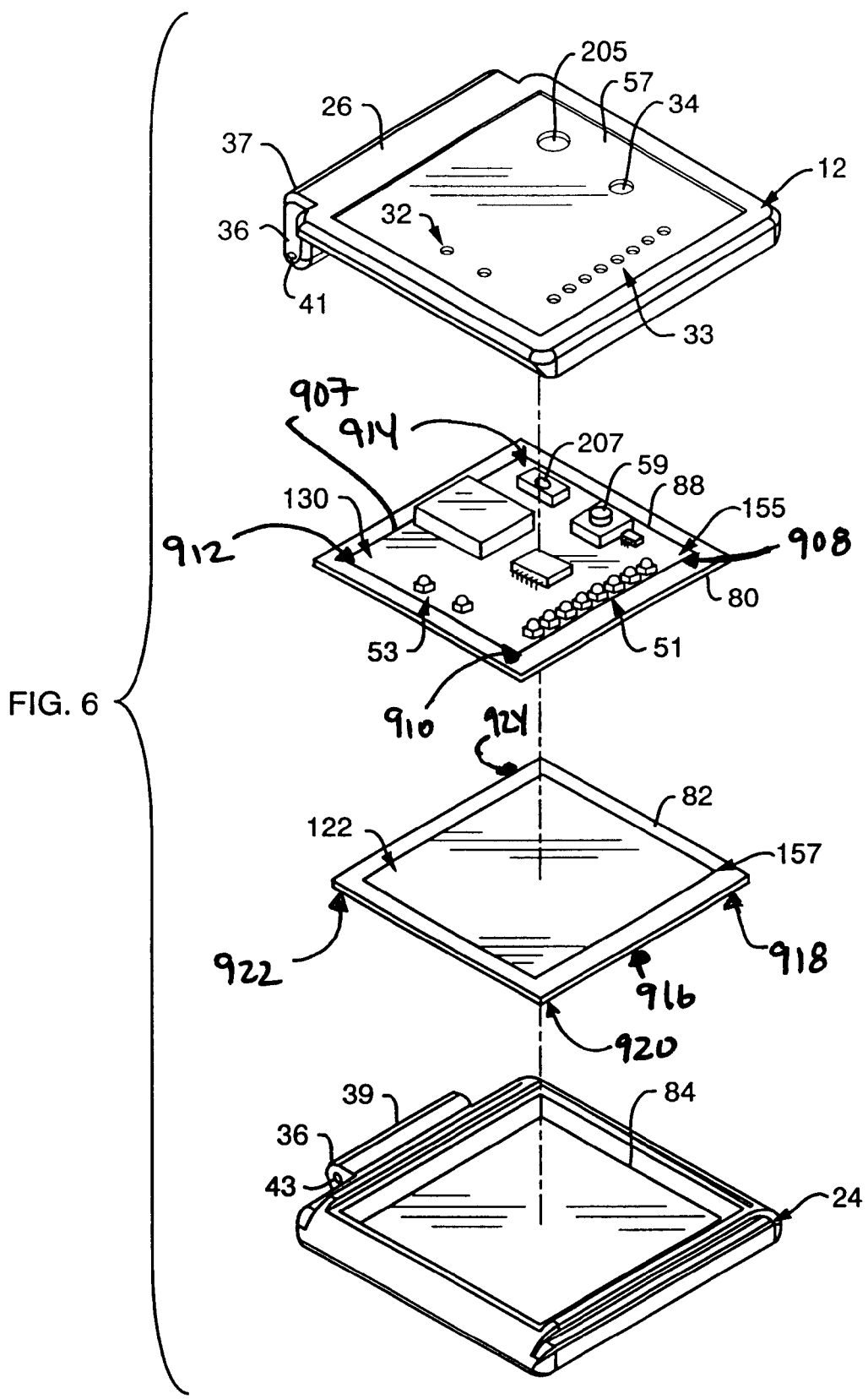
FIG. 6 is an exploded, schematic view illustrating the construction of the heater shown in FIG. 1, with the heat exchanger shown in FIG. 2 and the top indicator plate removed.

Although the following Detailed Description will proceed with reference being made to illustrative embodiments and methods of use, it will be appreciated by those skilled in the art that the present invention is not intended to be limited to these embodiments and methods of use. Rather, the present invention is intended to be viewed quite broadly as being defined only as set forth in the hereinafter appended claims.

DETAILED DESCRIPTION OF ILLUSTRATIVE EMBODIMENTS

FIGS. 1–12A, 12B and 15 depict a wearable infusion fluid heater 10, in which one embodiment of the heat exchanger 17 of the present invention may be used. Heater 10 comprises a hard plastic housing 12 in the form of two generally square-shaped members 24, 26 joined via a locking hinge mechanism 36. Hinge mechanism 36 comprises an upper hinge portion 37 and mating lower hinge portion 39. These hinge portions 37, 39 are pivotably connected to each other via conventional means (e.g., a bolt, screw, or similar means, not shown) fastened into the common opening through the portions 37, 39 formed when the portions 37, 39 are mated with each other and the respective openings 41, 43 of the portions 37, 39 are in coaxial alignment with each other. Openings 41, 43 extend longitudinally through the hinge portions 37, 39.

A rectangular indicator face plate 14 is slightly undersized relative to rectangular recessed area 57 of top plate 26 and is attached thereat via conventional means (e.g., glue or other type of bonding material) to the top plate 26. Indicator plate 14 includes a plurality of openings (collectively referred to by numerals 32,33) to permit viewing of light emitting diode (LED) indicators 51, 53, and opening 34 for permitting user access to and activation of alarm mute button 59, attached to the top side 88 of circuit board 155.

Similarly, plate 14 may include an opening 205 for permitting user access to and activation of heater on/off power button 207 attached to the top side 88 of circuit board 155. Alternatively, plate 14 may be replaced by a relatively thin, flexible membrane, having appropriate transparent portions (e.g., for viewing indicators 51, 53) and through which the buttons 59, 207 may be activated and deactivated.

Plate 14 also includes written/numerical descriptions of the information conveyed by activation of LED indicators 51, 53, and the functions that are toggled by buttons 59 and 207. More specifically, indicators 51 indicate the output temperature of the infusion fluid from the heater 10 in one degree increments from 35 degrees C. to 42 degrees C.

Activation of the "No Flow" LED of indicators 53 indicates that the flow rate of infusion fluid through the heater 10 is below a predetermined minimum desired therefor, while activation of the "Lo Batt" indicator LED indicates that the power level being supplied from the power supply 116 has fallen to a degree sufficient to inhibit proper operation of the heater 10. Likewise, although not shown in the Figures, a separate indicator LED may be provided on board 155, and displayed through the plate 14 for indicating if air is present in the flow path 43 through the heater 10.

When the heater 10 is in use (i.e., heating fluid to be infused to the patient), the housing 12 almost completely encloses a heat exchanger 17. The heat exchanger 17 according to this embodiment of the invention comprises a member 65 of unitary construction, and two flexible sheets 40, 42. Member 65 in this embodiment is made of plastic (e.g., polyester), and is formed by injection molding. Infusion fluid flow path 43 through the heater 10 is defined by the flexible sheets 40, 42 together with the member 65, and includes fluid inlet 20, fluid outlet 22, and serpentine channel 47 between inlet 20 and outlet 22. Inlet 20 comprises a female luer fitting for being mated to a corresponding male luer fitting (not shown) whereby to permit the heat exchanger 17 to receive, via tubing 600 connected to the corresponding fitting, an unheated flow of infusion fluid from an external infusion fluid source (not shown); outlet 22 comprises a male luer fitting for being mated to a corresponding female luer fitting 602 whereby to permit transmission, via tubing 604 connected to the corresponding female fitting, of the heated infusion fluid from the heater 10 to infusion situs 606 of the patient 608. A releasable strap mechanism (e.g., a hook and loop or adhesive tape fastening system) 610 permits the heater 10 to be worn by the patient adjacent the situs 606.

In this embodiment, the sheets 40, 42 are square, flexible, identically dimensioned, contact respective internal sides of flared portions 16, 30, 50, 52 of the member 65, and completely cover from opposite respective sides of the member 65 the channel 47. In this embodiment, each of the flexible walls 40, 42 is a highly flexible, polyester plastic film, sputter-coated with an outer bond-coating of acrylic, and is physically bonded (e.g., via ultrasonic welding) by this acrylic layer to the bond-coating of the acrylic outer layer on the member 65, but is not physically attached to any other part of the heater 10.

In use, the heat exchanger 17 is sandwiched between circuit boards 155, 157 such that the bottom and top surfaces 80, 82 of the boards 155, 157, respectively are in intimate contact with the flexible walls 42, 40, respectively. Board 157 is undersized with respect to a square recess 84 formed in plates 24 into which panel 157 fits. It should be understood that although not shown in the Figures, a similar recess is formed in the top plate 26 for receiving the top panel 155.

Panels 155, 157 preferably each comprise Thermal Clad Bond Ply® base layers (commercially available from The Berquist Company of Minneapolis, Minn.), to which are bonded respective the electronic components 100. More specifically, panel 155 may include a double-sided circuit board comprising two copper etch layers 120, 130 disposed upon and separated by a fiberglass substrate 132. Various of the electronic components of heater 10 are surface mounted or otherwise formed on and connected to etch layer 130. Etch layer 120 is connected to the etch layer 130 via appropriate conventional means (e.g., connection through holes, etc.) and comprises a resistive heating element. The resistive heating element 120 is physically separated from an aluminum or copper plate heat sink 136 by an electrically insulating, but highly thermally conductive layer 134. Layer 134 may comprise a ceramic-filled, glass-reinforced polymer material. When heater 10 is in use, layer 136 is in intimate contact with flexible wall 42. Layers 120, 130, 132, 134, and 136 are all laminated together to form a solid, single circuit panel 155.

Circuit board 157 comprises a respective double-sided circuit board made up of copper etch layers 122, 144 separated by a fiberglass substrate 142. Etch layer 142 is electrically connected to etch layer 130 via a connection wire (not shown), and various of the electronics 100 of the heater 10 are surface mounted or otherwise formed on and connected to etch layer 142. Etch layer 122 is connected to the copper etch layer 144 via appropriate conventional means (e.g., connection through holes, etc.) and comprises another resistive heating element. The resistive heating element 122 is physically separated from an aluminum or copper plate heat sink 138 by an electrically insulating, but highly thermally conductive layer 140 of the same construction as layer 134. When heater 10 is in use, layer 138 is in intimate contact with flexible wall 40. A connection wire (not shown) electrically connects the traces 130, 144. Layers 122, 138, 140, 142, and 144 are all laminated together to form a solid single circuit board 157.

Hinge mechanism 36 permits the plates 24, 26 to be rotated relative to each other from the closed position shown in FIG. 1, to an open position (not shown). The hinge mechanism 36 also includes a conventional releasable locking mechanism for locking the plates 24, 26 into the closed position when they are moved from the open position into the closed position (i.e., when sufficient force is applied to plates 24, 26 for moving the plates 24, 26 to the open position). In the closed position, the plates 24, 26 clamp onto and come into sealing engagement with the flanged portions of the heat exchanger and with top and bottom flexible walls 42, 40, respectively, so as to form an air and liquid tight seal that prevents communication to and from the internal portion of the heater 10 enclosed by the housing 12, except via the inlet and outlet of the heat exchanger 17. Also in the closed position, the lower surface 80 of panel 155 is urged and held in place by the housing 12 in contact with flexible wall 42 and the upper surface 82 of panel 157 is urged and held in contact with flexible wall 40. In the open position of the housing 12, the circuit board members 155, 157 and the heat exchanger 17 may be accessed and removed from the housing 12. It is important to note that the heat exchanger 17 is not physically bonded to the rest of the assembly 10. Thus, when the clamping forces provided to the heat exchanger 17 by the housing 12 when the housing 12 is in its closed, locked position, are removed (i.e., when the hinge mechanism 36 is unlocked, and the plates 24, 26 are in the open position), the heat exchanger 17 may be disposed of and replaced with a fresh (i.e., unused) replacement heat exchanger. Additionally, although not shown in the Figures, in use, the assembly 10 is covered with an outer plastic contamination-preventing cover which may also be removed, discarded, and replaced, after use of device 10 on a patient. Thus, the assembly 10 may be reused on another patient, without substantial risk of contamination or other biohazard to that subsequent patient.

Figure 7:
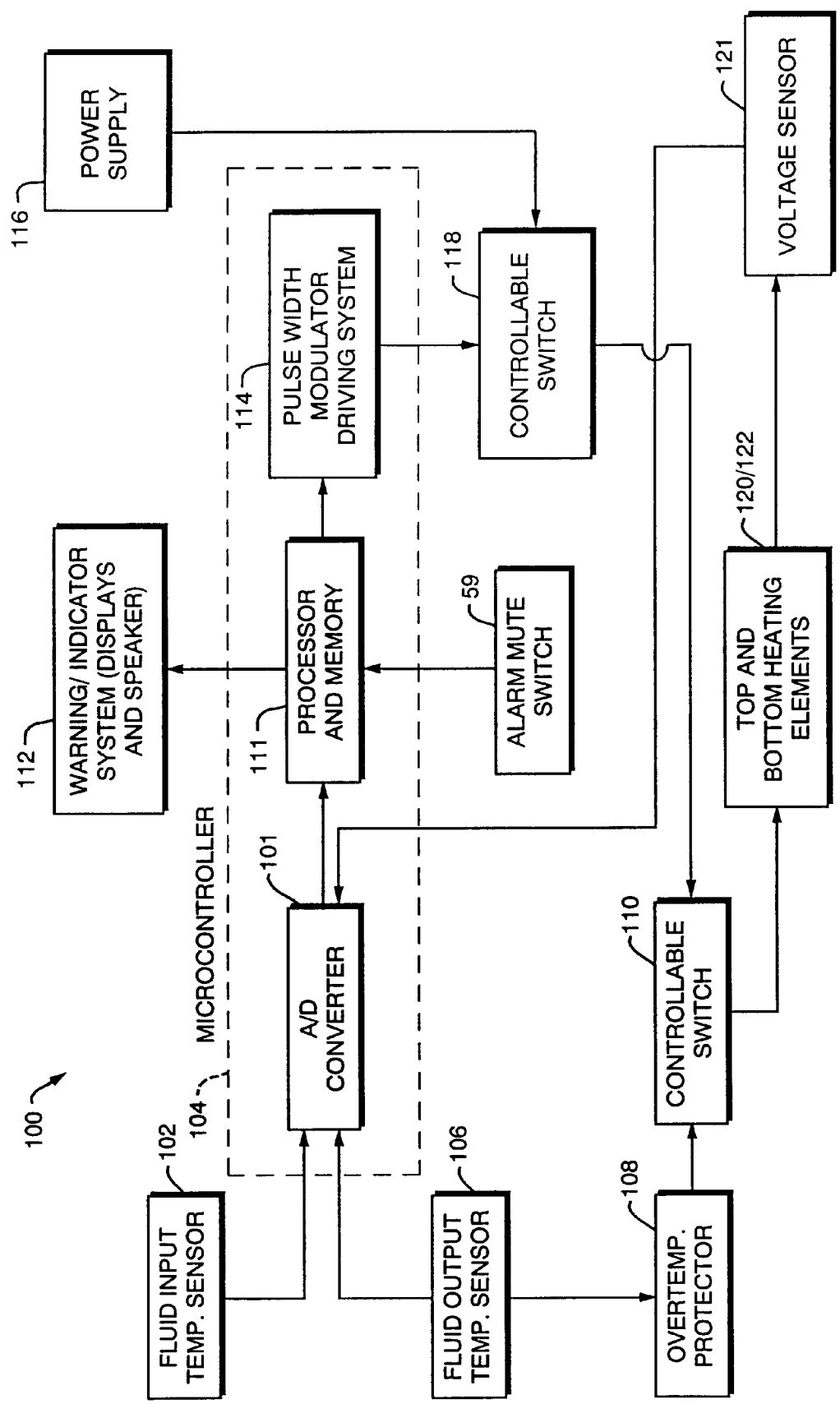
FIG. 7 is a highly schematic, functional block diagram of the electronics used in the heater shown in FIG. 1.
Figure 8:
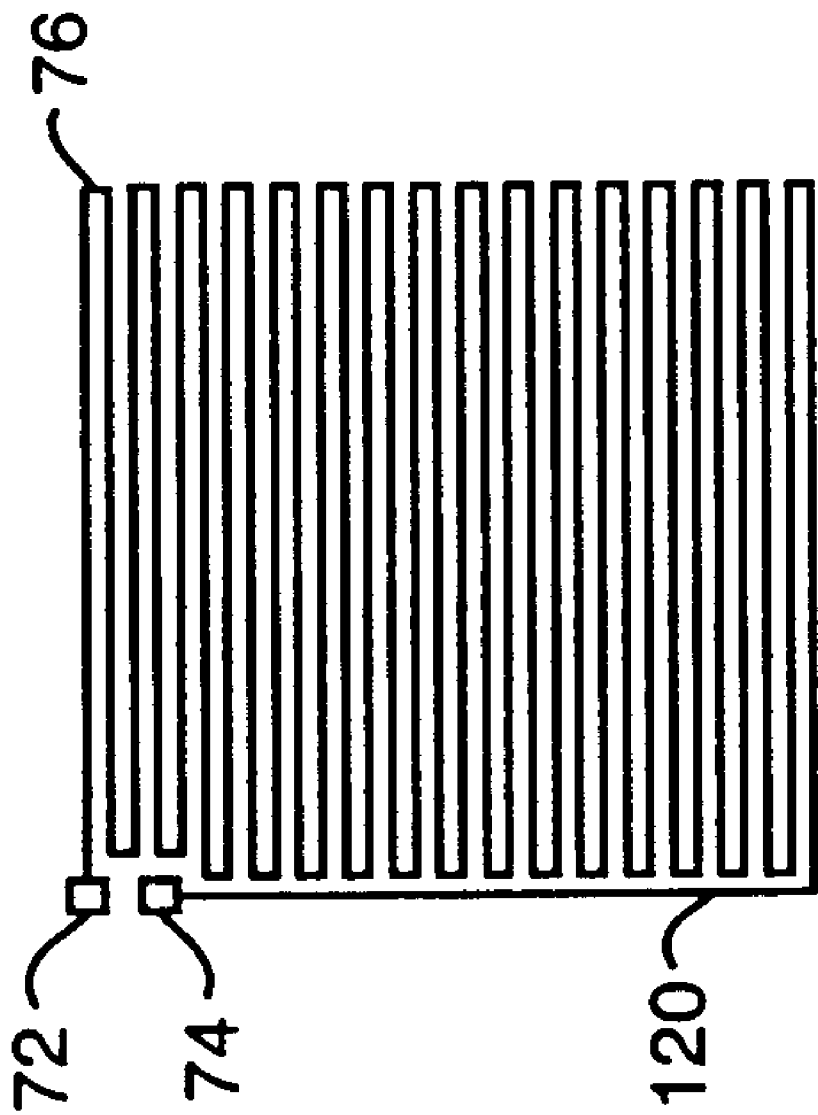
FIG. 8 illustrates the electrically conductive etchings used to heat the infusion fluid in the heater shown in FIG. 1.

FIG. 8 shows the copper trace pattern comprising heating element 120. It should be understood that although not shown in the Figures, heating element 122 (e.g., shown in schematic form in FIG. 6) comprises the same trace pattern. As shown in FIG. 8, element 120 comprises a plurality of copper trace turns 76, and two connector pads 72, 74, one of which is connected to the controllable switch 110 (FIG. 7), and the other being connected to ground potential. Energizing of the elements 120, 122 with electrical power from source 116 causes the heating elements 120, 122 to heat up, and this heat is supplied via heat conduction through the layers 134, 136, 138, and 140 to the heat exchanger 17, and thence into the fluid flowing through the flow path 43. The construction of layers 120, 122, 134, 136, 138, and 140 is such that substantially uniform heating is applied to the fluid flowing through flow path 43. Thus, elements 120, 134, and 136 may be said to constitute a single conductive heating element, and elements 122, 138, and 140 may be said to constitute another such heating element.

The electronic components 100 of the heater 10 comprise a single chip microcontroller 104. Microcontroller 104 may comprise a 16C715 chip available from Microchip Technology, Inc. of Chandler, Arizona, and has integrated circuits for implementing analog-to-digital converter 101, processor and associated ROM/RAM memory 111, and pulse width modulation power driver control system 114 functions. It should be appreciated that although not shown in FIG. 7, power supply 116 may comprise a plurality of power supplying circuits (i.e., for supplying different voltages and currents appropriate for powering the different types of circuits comprising the components 100 functionally represented in FIG. 7), and supplies power to microcontroller 104, temperature sensors 102, 106, over-temperature protection circuit 108, and mute switch 59, based upon the current state of the power switch 207 (i.e., whether it is in an "on" state or an "off" state). Power supply 116 may comprise a battery power supply system, and/or may rectify alternating current (AC) received from an external source (not shown) via an external connection (also not shown) to generate direct current (DC) suitable for supply to the circuits comprising components 100. It should be appreciated that the power supply button 207 may be replaced by a power switch (not shown) that is part of the AC power connection.

Converter 101 receives analog voltage signals from infusion fluid input and output temperature sensors 102, 106. These sensors 102, 106 may comprise respective thermistors that are connected to copper etch pattern 130 and positioned directly above the inlet portion 90 and outlet portion 92, respectively, of channel 47. These signals from the sensors 102, 106 are digitized by the converter 101 and are supplied to the processor and memory 111, which then processes the digitized signals, in a manner that will be described more fully below, to determine the input and output temperatures of the infusion fluid (i.e., the temperature of infusion fluid at inlet 90 prior to being heated by the heater 10, and at outlet 92 after being heated by the heater 10, respectively).

Converter 101 also receives analog input signals from voltage sensor 121. These signals from the voltage sensor 121 indicate the instantaneous voltage across one or both of the heating elements 120, 122, are also digitized by the converter 101, and the digitized signals are supplied by the converter 101 to the processor 111. As will be described more fully below, processor 111 utilizes them together with the digitized signals from the sensors 102, 106 to generate control signals for controlling the warning/indicator system 112 and pulse width modulated signal generator 114. Of course, if the components 100 are appropriately modified, sensor 121 may be eliminated, and the voltage from one or both of the heating elements may be determined directly by supply of the digitized voltage(s) across the element(s) to the processor 111. System 112 includes the indicators 32, 33 and a speaker system (not shown) for sounding audible alarms. The pulse width modulated signals generated by system 114 control the state of switch 118, which switch 118 controls supply of power from supply 116 to the heating elements 120 and 122. Alarm mute switch 59 permits a user (not shown) to selectively disable the processor 111 from being able to command the system 112 to generate audible alarms.

Over-temperature protection circuit 108 deactivates heating elements 120, 122 when the output temperature of the infusion fluid exceeds a predetermined maximum temperature (e.g., 42 degrees C.), by controlling switch 110 to prevent power from being supplied to the elements 120 and 122; so long as the temperature at the outlet 92 of the channel 47 remains below this maximum threshold, the protector 108 maintains the switch 110 in a state that does not prevent the supply of power to the elements 120, 122. Each of switches 110, 118 may comprise transistor-based switching circuits.

Figure 9:
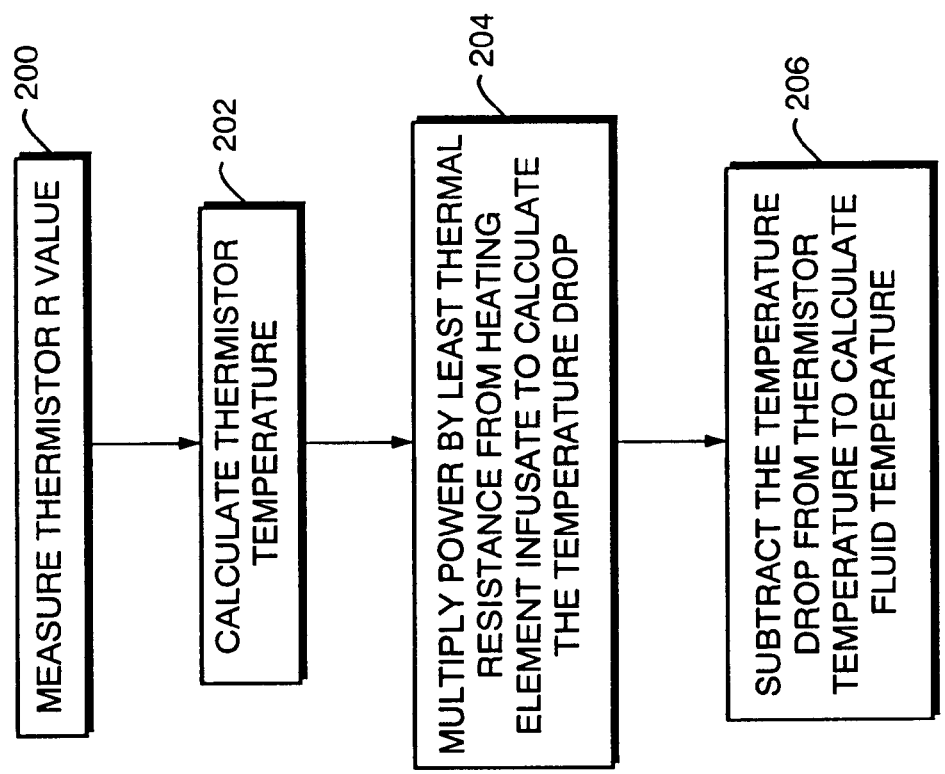
FIG. 9 is a flowchart of the fluid temperature measurement method used in the heater shown in FIG. 1.

Turning now to FIG. 9, one method used by processor 111 to determine the input fluid temperatures using the digitized signal from the sensor 102 will now be described. In the method, the digitized signals from the 102 are first used by the processor 111 to calculate the present resistance of the thermistor comprised in the sensor 102. (See, block 200). As is known to those skilled in the art, one of the properties of a thermistor is that its resistance changes in a predictable way with changes in its temperature. Thus, the circuit comprising the sensor 102 must be constructed in such a way as to permit the voltage signals supplied by the sensor 102 to be truly indicative of the present resistance of the thermistor comprised in the sensor 102. The relationship between the output voltage of the sensor 102 and the resistance of the thermistor comprised in the sensor 102 may be determined empirically, and the processor and memory 111 uses this relationship to determine the present resistance of thermistor based upon the output voltage of the sensor 102. Likewise, the relationship between the present resistance of the thermistor of sensor 102 and its temperature may be determined empirically, and the processor and memory 111 may use this relationship to calculate the present temperature of the thermistor, once the present resistance of the thermistor has been determined. (See, block 202)

However, during use of the heater 10, the present temperature of the thermistor of sensor 102 is higher than the present temperature at the inlet 90. This is due to the thermistor's relatively close proximity to the heating element 120 and the drop in temperature that occurs from the sensor 102 to the infusion fluid in the inlet 90 of the channel 47, due to the thermal resistance that exists in the layers 42, 134, and 136 (the thermal drop across layer 132 is substantially negligible). The processor 111 determines the actual temperature at the inlet 90 by calculating this temperature drop and subtracting the temperature drop from the calculated temperature of the thermistor of sensor 102.

More specifically, processor 111 calculates the temperature drop by calculating heating energy being output by the heating element 120 based upon the duty cycle of the pulse width modulated signals that the processor 111 commands the driving system 114 to generate, and then multiplies the heating energy by the thermal resistance from the heating element 120 to the inlet 90. The heating energy being output by the element 120 is calculated based upon the relationship between the total electrical power (derived from the pulse width modulated signals' duty cycle) delivered to the heating element 120 and the heating energy supplied from the heating elements 120 as a result of supply of said power, which relationship is empirically determined and preprogrammed into the processor 111. Likewise, the thermal resistance of the layers 42, 134, and 136 is determined empirically, and preprogrammed into the processor 111. It is assumed for purposes of these calculations that all of the heating energy supplied by the element 122 is absorbed by elements 40, 138, 140 and the fluid in the flow path. Device 10 is constructed so as to permit this to be an accurate assumption. Once the total temperature drop across layers 42, 134, and 136 is determined, the temperature drop is subtracted out from the temperature of the thermistor of sensor 102 to yield the temperature of the fluid at the inlet 90.

The same procedure as that discussed above for determining the temperature of the fluid at the inlet 90 is also used by the processor 111 to determine the temperature of the fluid at the outlet 92. Of course, it is the digitized voltage signal from sensor 106, rather than that from sensor 102, that is used by processor 111 to determine the output fluid temperature. Once the output fluid temperature is determined, processor 111 generates signals that activate an appropriate one of the LEDs of system 112 to indicate this temperature. Additionally, if the output fluid temperature exceeds a predetermined maximum therefor (e.g., 42 degrees C.), the processor 111 may cause the system 114 to immediately cease heating of the fluid by heating elements 120, 122, and cause a speaker comprised in the system 112 to generate an audible warning.

Figure 10:
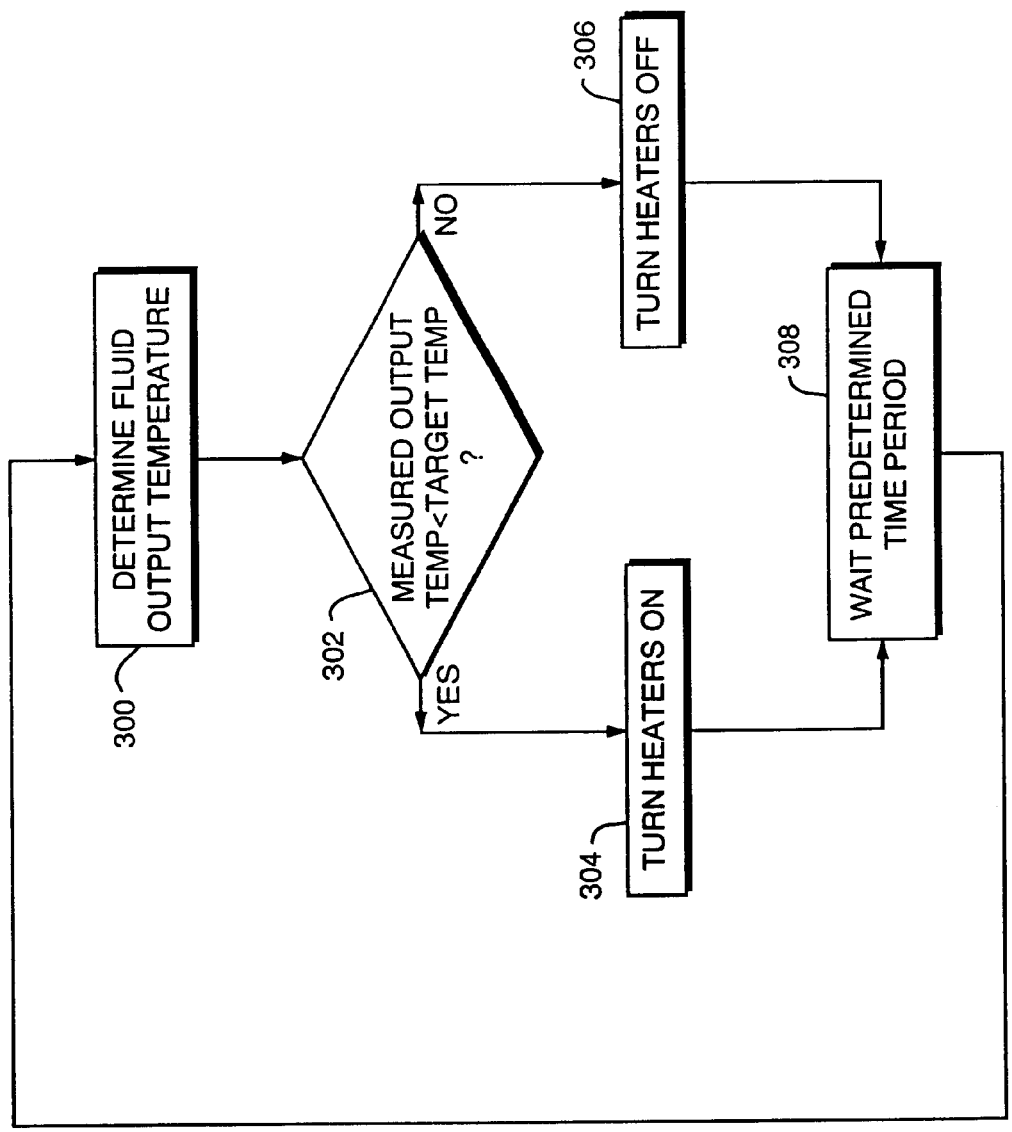
FIG. 10 is a flowchart of one fluid heating control method that can be used in the heater shown in FIG. 1.

FIG. 10 illustrates steps of one method that can be used by the processor 111 to control heating of the fluid by the heater 10. According to this method, once the output fluid temperature is determined using the aforedescribed procedure (see block 300), the processor 111 determines whether the output fluid temperature is less than a predetermined target output fluid temperature (e.g., 40 degrees C.), and if the output temperature is less than this target temperature, the processor 111 causes the system 114 to initiate or maintain heating of the fluid in the flow path 43 by the heating elements 120, 122 (See, blocks 302 and 304). Alternatively, if the processor 111 determines that the output fluid temperature is greater than the target temperature (but less than the predetermined maximum temperature), the processor 111 may command the system 114 to cease heating of the fluid in the flow path 43 by the heating elements 120, 122. (See, block 306). There-after, the processor 111 may wait a predetermined time period (e.g., several milliseconds), and then begin the control process again at block 300.

Figure 11:
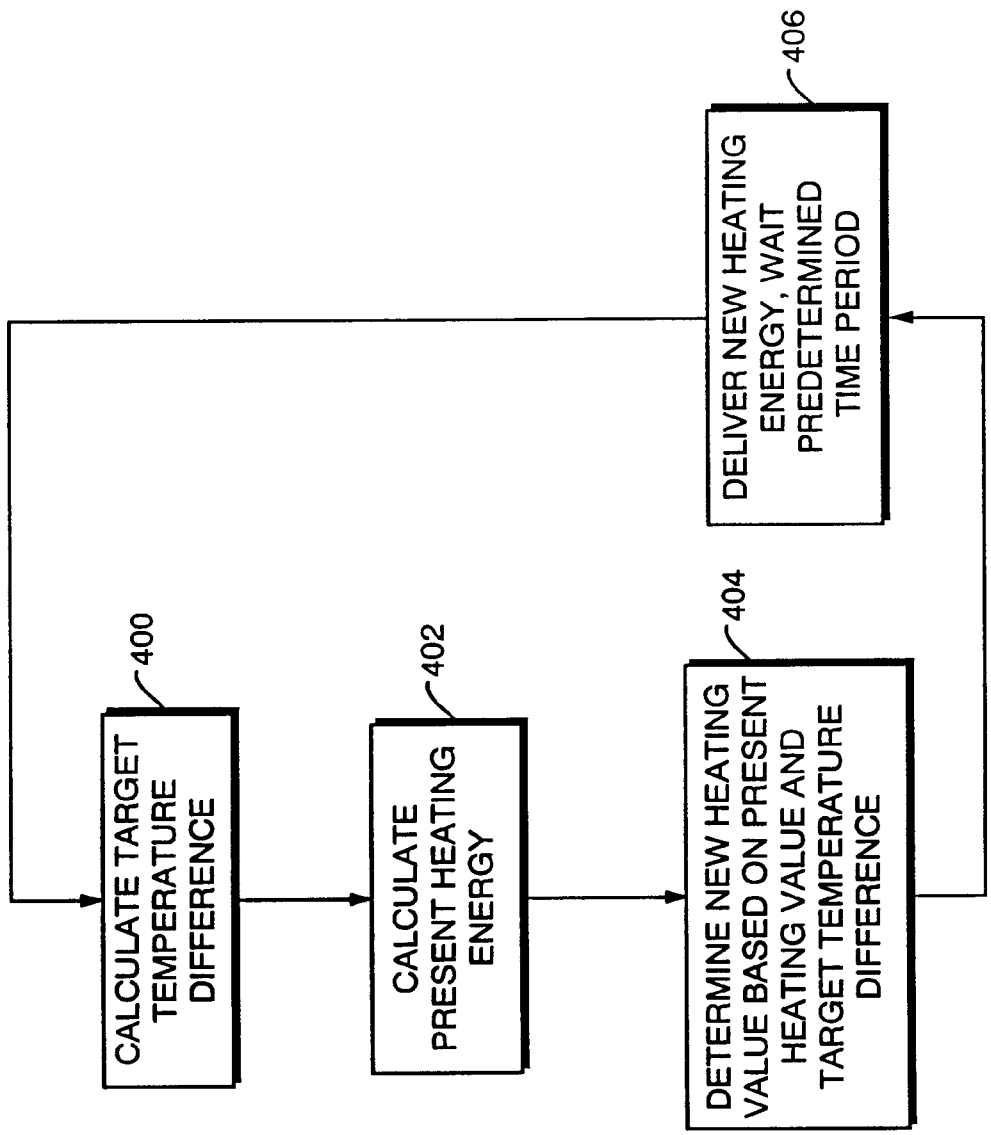
FIG. 11 is a flowchart of another fluid heating control method that can be used in the heater shown in FIG. 1.

Steps of an alternate method that may be used by the processor 111 to control the heating of the infusion fluid in the flow path 43 by the heating elements 120, 122 is shown in FIG. 11. Processor 111 begins this method by calculating the difference between the output fluid temperature determined in the manner described above, and a target temperature therefor (e.g., 40 degrees C.). (See, block 400) The processor 111 then calculates the heating energy being output by both the heating elements 120, 122, based upon the duty cycle of the pulse width modulated signals supplied by system 114 to switch 118. (See, block 402). The processor 111 then calculates the heating energy required to be output by the heating elements 120, 122 to raise the output temperature of the fluid to the target temperature, based upon an empirically determined relationship between the amount of heating energy supplied by the heating elements 120, 122 and expected temperature rise in the output temperature of the fluid, assuming a predetermined flow rate of the fluid through the flow path 43 (e.g., between about 2550 and 3600 ml/hour). (See, block 404) This relationship is preprogrammed into the processor and memory 111. Once the processor 111 determines this new heating energy, it controls the system 114 so as to cause same to output pulse width modulated signals having a duty cycle that causes the heating elements 120, 122 to output the new heating energy. (See block 406). The processor then waits a predetermined amount of time (e.g., several milliseconds), and begins the process again at block 400.

Figure 12A:
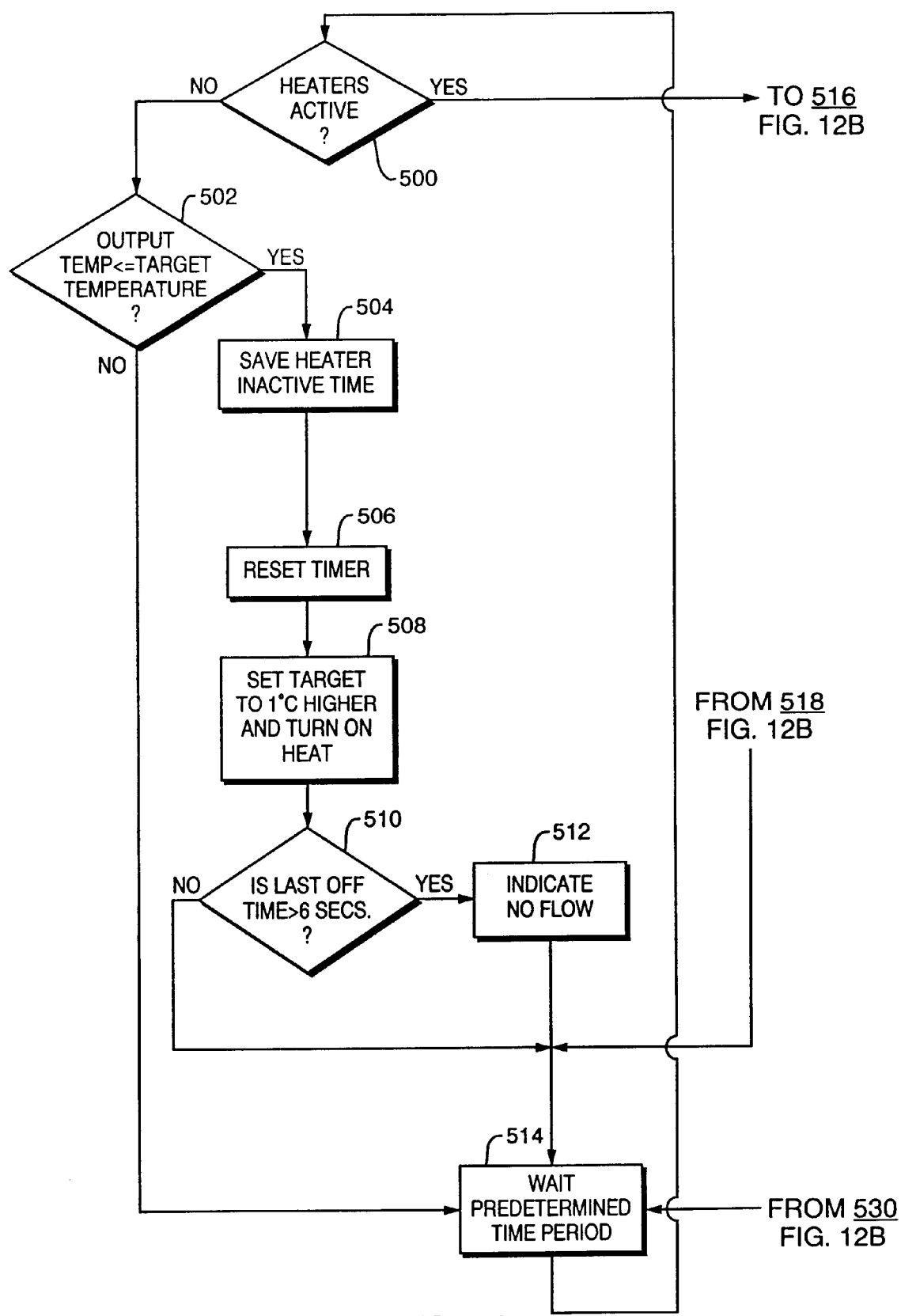
FIGS. 12A and 12B are flowcharts of a process used in the heater shown in FIG. to determine whether gas is present in, and/or fluid flow rate through the heat exchanger's fluid flow path is below a desired minimum value therefor.
Figure 12B:
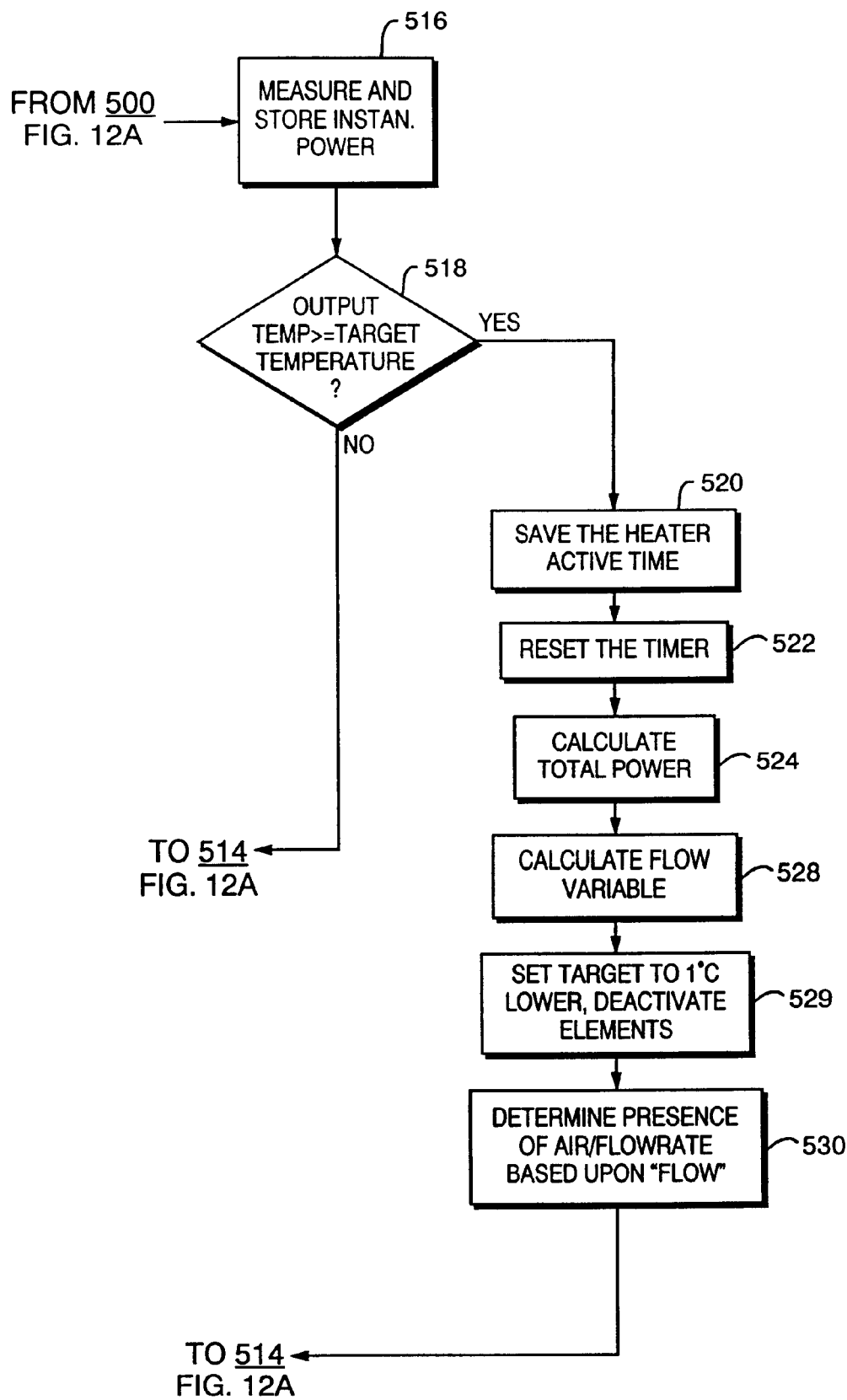

FIGS. 12A and 12B illustrate steps of one method used by the processor 111 to determine whether air is present in the flow path 43 and/or that the flow rate of fluid in the flow path 43 is below a desired minimum threshold value therefor. Processor 111 begins this method by determining whether the heating elements 120, 122 are in an active state (i.e., being energized by the power source 116), based upon the pulse width modulated signals being generated by the system 114. If the heating elements 120, 122 are in an active state, the instantaneous power being delivered to heating elements 120, 122 is calculated by the processor 111 based upon the electrical resistances of the heating elements 120, 122 and the instantaneous voltages across the heating elements sensed by the voltage sensor 121. The electrical resistances of the heating elements 120, 122 are equal to each other, and are preprogrammed in the processor 111. The processor 111 then continues the process of FIGS. 12A and 12B by determining whether the output fluid temperature, determined as described above, is greater than or equal to a predetermined target temperature (e.g., 40 degrees). If the output fluid temperature is at least equal to the target temperature, the amount of time that the heaters 120, 122 have been most recently active is saved by the processor in memory (see block 520), and a timer used to determine the most recent active time of the heating elements 120, 122 is reset. (See, block 522) The total power delivered to the heating elements 120, 122 is then calculated based upon the previously stored instantaneous power and the length of time of the previous period of activation. Thereafter, a time constant (determined empirically and preprogrammed into the processor 111), equal to the time the heater 10 would take based upon the total power supplied to the heating elements 120, 122 during the most recent activation period to heat the infusion fluid from the input fluid temperature to the target temperature if the fluid in the flow path 43 is not flowing, is subtracted from the length of time of the most recent period of activation of the heating elements 120, 122. (See, block 524). The result of this subtraction is then used to determine whether air is present in the flow path 43 and/or the flow rate of the fluid through the flow path 43 is less than desirable. (See, block 530). Prior to making the determination at block 530, however, the processor 111 sets the target temperature to a value that is one degree C. lower than that to which it is presently set, and deactivates the heating elements 120, 122. (See, block 529)

At block 530, the processor 111 determines whether the value of the "flow" variable (i.e., the time constant subtracted from the length of the most recent period of activity of the heating elements 120, 122) is less than zero, and/or is at zero, or between zero and a minimum acceptable flow rate value. If the calculated flow variable is less than zero, the processor 111 determines that air is present in the flow path 43, since air can be is heated more quickly that the fluid. If the calculated flow variable is at zero or between zero and the minimum flow rate value, the processor 111 determines that the flow rate through the flow path 43 is less than desirable. In either case, the processor 111 generates signals which cause appropriate LED indicator(s) of system 112 to be activated and/or audible warnings to be sounded.

After either carrying out the process steps of block 530 or determining at block 518 that the output fluid temperature is less than the target temperature, the processor 111 then waits a predetermined time period (block 514), and returns to carry out the step at block 500.

If at block 500, the processor 111 determines that the heating elements 120, 122 are not activated, the processor 111 proceeds to determine whether the output fluid temperature is less than or equal to the target temperature. If so, the processor 111 saves in memory the current amount of time that the heating elements 120, 122 have been deactivated and resets the timer used to determine this time. (See, blocks 502, 504, and 506). Thereafter, the processor 111 sets the target temperature to be one degree higher that the value to which it was previously set (block 508), and determines whether the current time of deactivation saved at block 504 is greater than an empirically determined amount of time (e.g., 6 seconds) within which the outlet 92 temperature should cool to the target temperature if sufficient fluid flow is present in the flow path 43. (See block 510) If the current time of deactivation is greater than this predetermined amount of time, the processor 111 determines that the flow rate in the path 43 is less than desirable, and signals this condition in the aforedescribed manner. (See block 512)

After processing the steps at block 512, or if either the output fluid temperature is determined at block 502 to be greater than the target temperature or the current time of deactivation is determined at block 510 to be less the predetermined time period, the processor 111 undertakes the previously described action at block 514. After processing the action at block 514, the processor 111 loops back to begin the process of FIG. 12A and 12B again at decision block 500.

Over-temperature protection circuit 108 generates control signals which control the state of switch 110 based upon the voltage signals supplied from the sensor 106. Circuit 108 may comprise an operational amplifier configured as a comparitor for comparing the voltage signals from the sensor 106 to a reference voltage signal indicative of a maximum desired output fluid temperature (e.g., 42 degrees C.). The protector circuit 108 generates signals based upon this comparison that cause the switch 110 to stop flow of power to the elements 120 and 122 if the voltage signals from the sensor 106 indicate that the output fluid temperature exceeds that maximum temperature. Although not shown in the Figures, the protector circuit 108, instead of the processor 111, may provide signals to system 112, in the event that the output fluid temperature exceeds the maximum temperature, to cause system 112 to indicate presence of a fault condition in the heater 10 and to provide an audible warning of same. The protection circuit 108 and switch 110 are connected to the circuit traces 144 and are disposed on substrate 142.

Processor 111 may also be adapted to detect when the power being supplied by supply 116 drops below a predetermined minimum threshold therefor necessary for proper operation of the heater 10, and to generate control signals for causing warning system 112 to indicate same by activating the "Lo Batt" LED and sounding an audible warning using the speaker comprised in system 112.

In this embodiment of the invention, the thickness of the portion of the member 65 defining the channel may be about 0.032 inches, the width 58 of the channel 47 may be 0.28 inches, and the thickness 60 of the fluid channel dividers of member 65 may be about 0.060 inches. The total length of the heat exchanger 17 from the end 54 of the inlet to the end 56 of the outlet 22 in this embodiment may be about 3.71 inches and the length from one flared end (e.g., 16) to an opposite, flared end (e.g., 30) may be about 2.25 inches. Each of the flexible walls 40, 42 may be 0.002 inches thick. Each of the aluminum plates 136, 138 may have a thickness of 0.040 inches and may be 1.75 inches in length and width.

Figure 13:
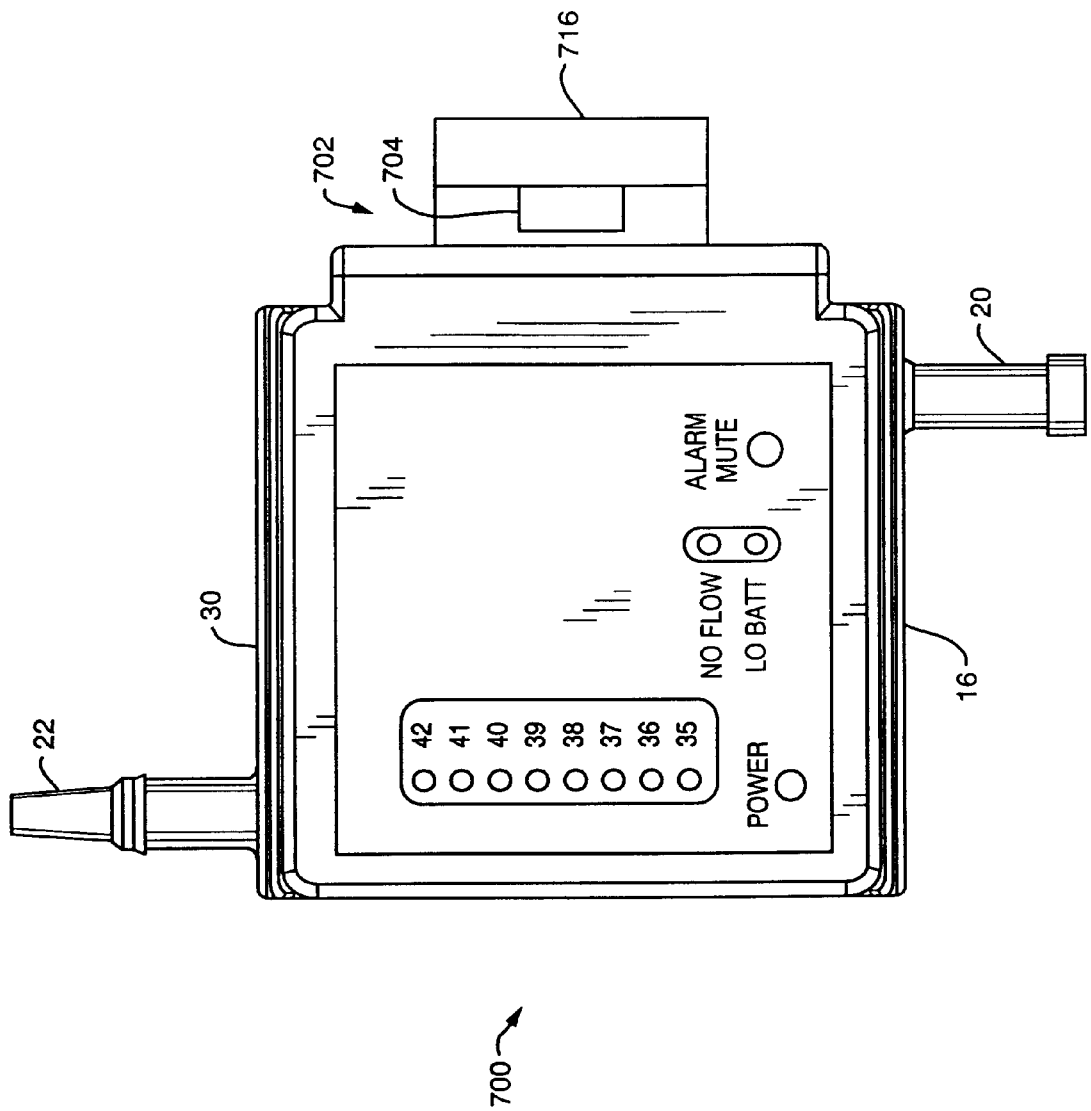
FIG. 13 is an outside perspective view of a variation of the heater shown in FIG. 1, which variation includes a controllable valve for stopping fluid flow through the heater if gas is present in and/or fluid flow through the heat exchanger is below a desired minimum therefor.
Figure 14:
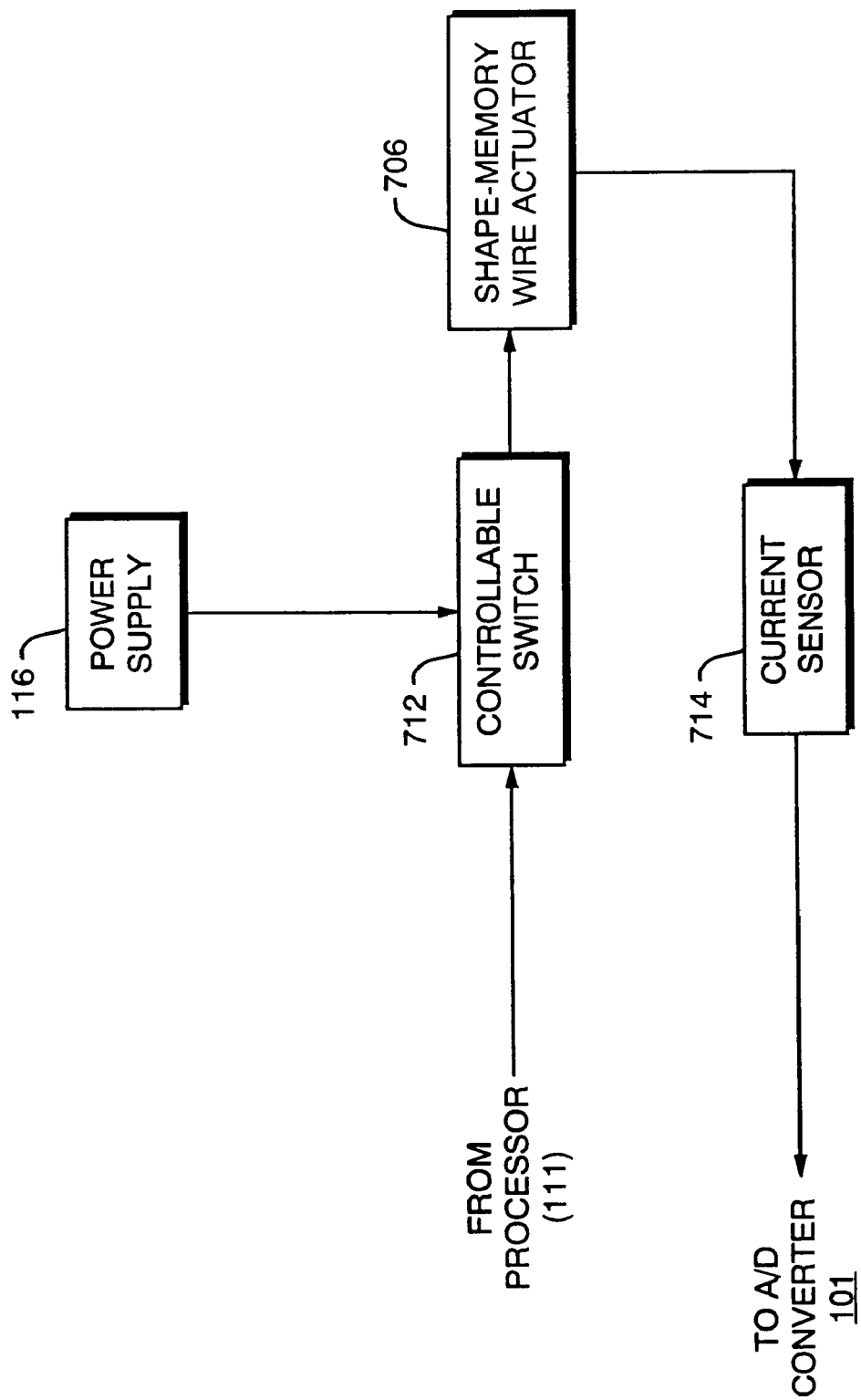
FIG. 14 is a highly schematic functional block diagram of electronics of the controllable valve system used in the variation of FIG. 13.
Figure 15:
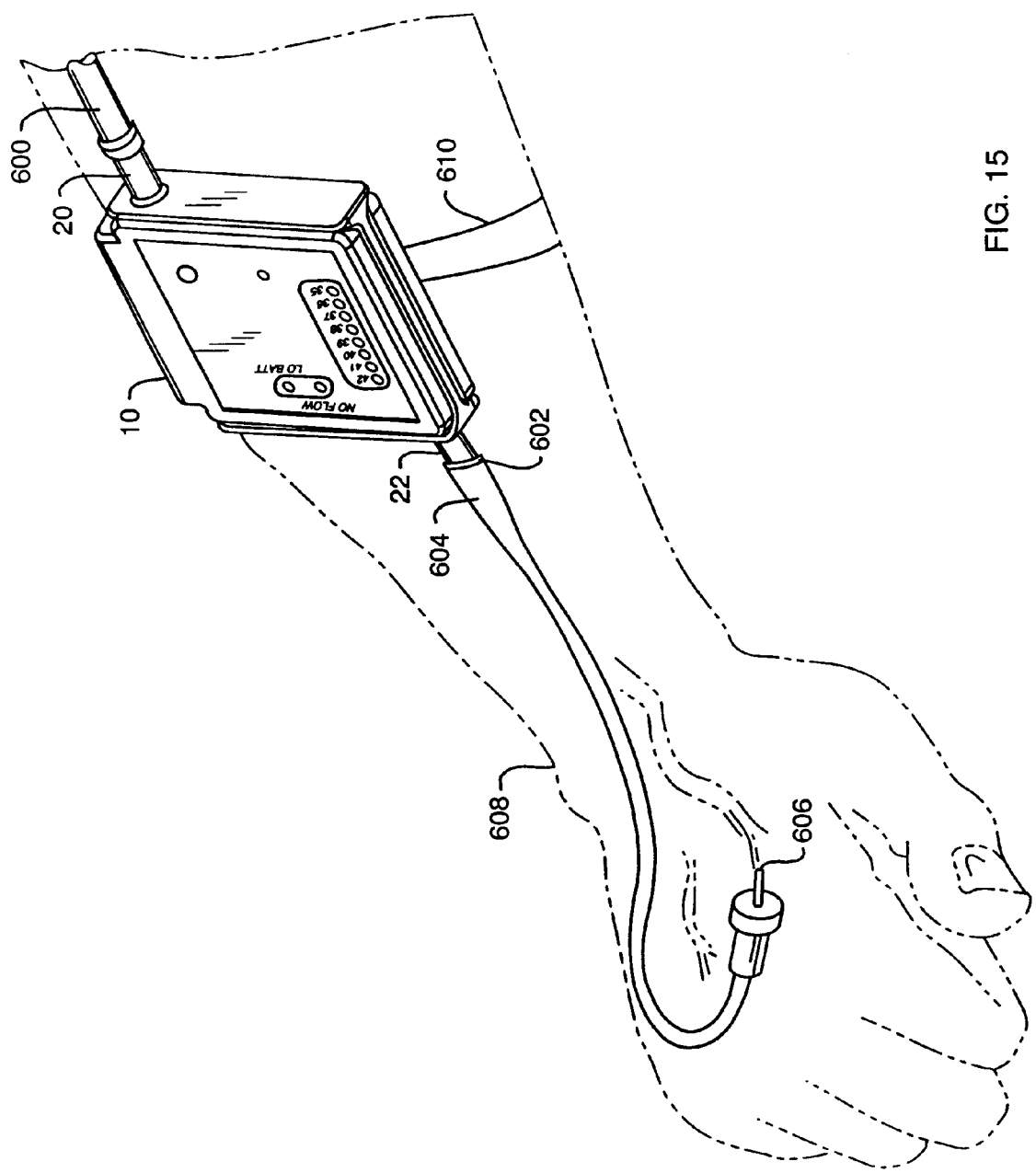
FIG. 15 shows the heater shown in FIG. 1 in use, being worn by a patient and delivering heated infusion fluid to a patient's infusion situs.
Figure 16:
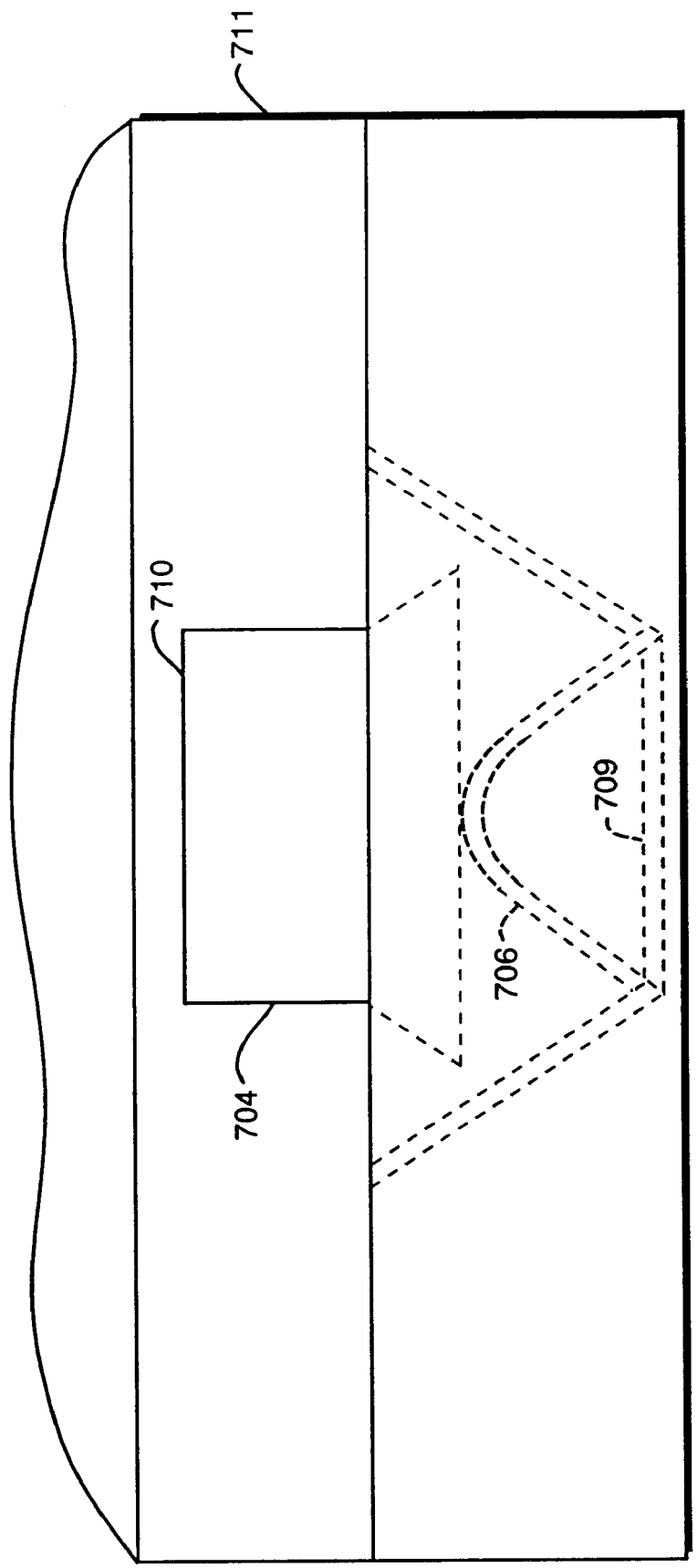
FIG. 16 is a schematic representation of the piston, tube choke channel, and memory wire actuator of the valve system of the variation of FIG. 13.

Turning now to FIGS. 13–14 and 16, a variation 700 of the heater 10 shown in FIGS. 1–12A, 12B and 15 will now be described. In variation 700, the positions of various of the indicators are different from those of heater 10. Variation 700 also includes a valve system 702 comprising a piston member 704 (shown partially in ghost) that is actuated by a plastic spring 706 based upon changes in shape and/or length of a shape memory wire 709 (e.g., a nitinol-type wire) Both the spring 706 and wire 709 are shown in ghost in FIG. 16. The wire 709 changes shape and/or length when its temperature exceeds a transition temperature for such change, and returns to its original shape and/or length when its temperature passes below that transition temperature. More specifically, in variation 700, the tubing connecting the output port 22 to the patient's infusion situs may be made to pass through a choke collar 711 attached to the housing 12. The wire 709 may be connected to the power source 116 via a controllable switch 712 whose state is controlled by control signals supplied thereto from processor 111. When power is supplied to the wire 709, the wire 709 heats up to transition temperature and changes shape so as to cause the spring 706 to impinge upon and push the piston 704. This causes a surface 710 of the piston to impinge upon and squeeze the tubing running through the choke collar sufficiently to cut off fluid flow through the tubing. A current sensor 714 may be connected to the wire (by conventional means, not shown) to sense the current flowing through the wire 709 and to provide the sensed current information to the processor 111 so as to enable the processor 111 to prevent overheating of the wire 709. After the power is cut off from the wire 709, the wire 709 cools to below its transition temperature and returns to its initial, relaxed shape and/or length (which in the variation of FIG. 16 is longer than that which is shown therein) that permits the fluidic pressure and natural elasticity of the tubing to force the piston out from the choke collar into housing portion 716 containing the spring 706 and wire 709. The processor 111 may be programmed to actuate the valve system in the event that the processor 111 detects presence of air or inadequate fluid flow rate in the path 43.

In another embodiment of the present invention, at least one 40 of the flexible walls of the heat exchanger 17 may be porous and hydrophobic. In this alternate embodiment, the wall 40 may be made of Gortex™ expanded polytetrafluoroethylene. The size of the pores in wall 40 may be approximately 0.45 micron in diameter, although, as will be appreciated by those skilled in the art, the pores in wall 40 may be differently sized without departing from this embodiment of the present invention. In this alternate embodiment, the sheet 40 may be thicker than the other sheet 42 of the exchanger 17, and the sheet 42 may be made of a polycarbonate material. The size and number of the pores of the membrane 40 are selected to permit gas (e.g., dissolved air) in the fluid to pass through the pores of the membrane 40 and prevent fluid in the exchanger 17 and bacteria from passing through the pores. Advantageously, this permits gas that is entrained and/or dissolved in the fluid to be continuously purged from the exchanger 17 through the pores of the porous membrane 40 during heating of the fluid in the exchanger 17, and to be vented from the fluid and exchanger during "priming" of the heat exchanger so as to remove gas bubbles in the fluid prior to infusion of the fluid to the patient. As will be appreciated by those skilled in the art, the pressure and/or flow rate of fluid in the flow path 43 should be maintained at sufficient levels during infusion of fluid to the patient to minimize the incorporation of gas into the infusion fluid. Advantageously, by using the porous membrane 40 in the heat exchanger 17 during priming of the exchanger and heating of the fluid, the amount of gas purged and vented from the fluid may be substantially improved compared to the prior art.

Figure 24:
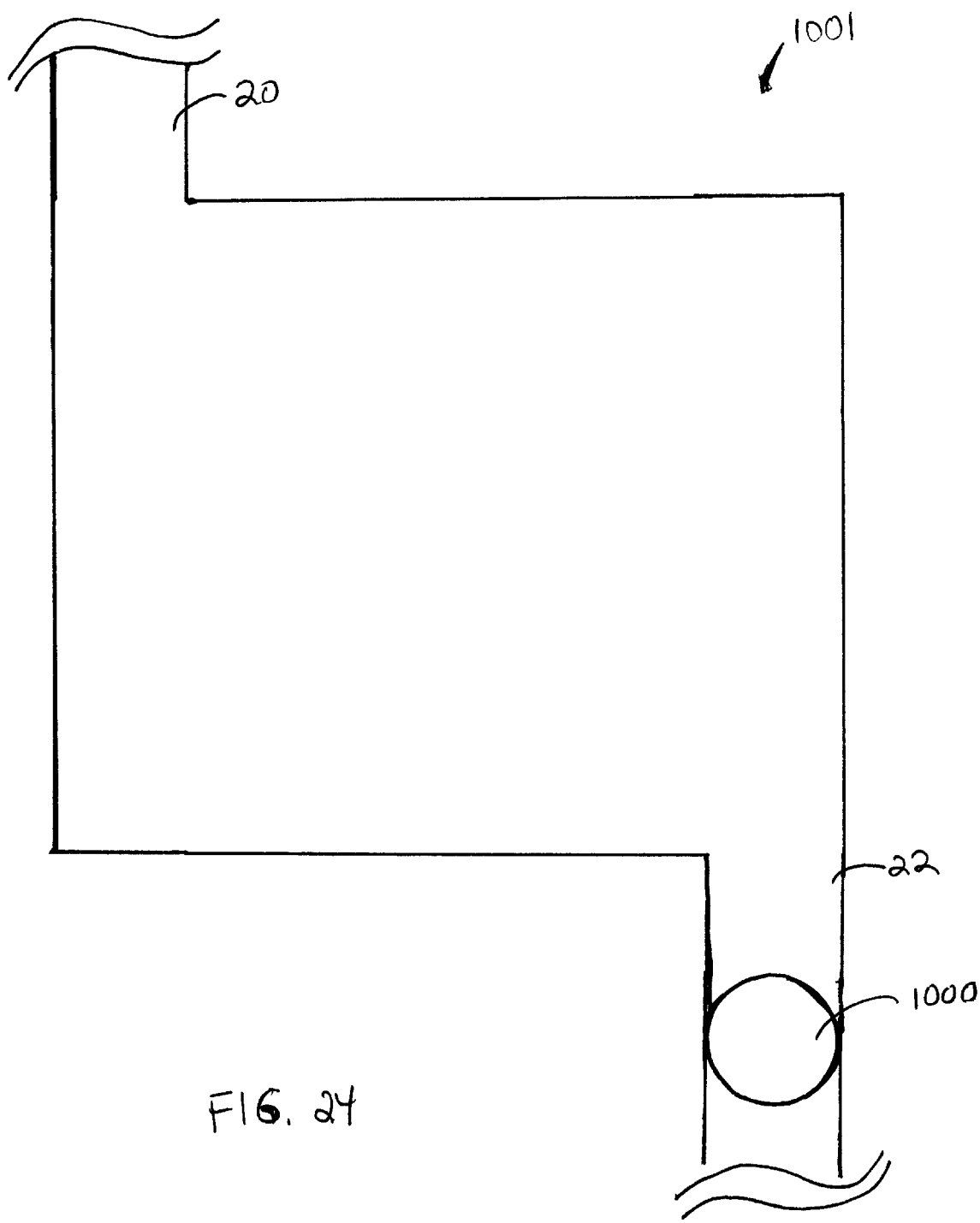
FIG. 24 is a highly schematic diagram illustrating another embodiment of the present invention.

FIG. 24 illustrates a variation 1001 of the previously described embodiment of the heat exchanger of the present invention wherein at least one membrane 40 is porous. Unless specifically stated to the contrary herein, it should be understood that the construction and operation of the embodiment 1001 are substantially identical to the construction and operation of said previously described embodiment.

In heat exchanger 1001, a pressure regulating valve 1000 is placed into the fluid flowpath out of the exchanger 1001 at the fluid outlet 22. Valve 1000 is constructed so as to ensure that, when the infusion fluid input into the exchanger 1001 has a sufficiently large pressure, adequate fluid pressure is maintained in the heat exchanger 1001 to ensure that ambient air is prevented from flowing into the exchanger 1001 through the pores of the porous membrane of the exchanger 1001 and becoming entrained in the infusion fluid flowing in the exchanger 1001. The infusion fluid input to the exchanger 1001 may be caused to exhibit such a sufficiently large pressure by e.g., employing an appropriately constructed fluid column (not shown) to supply the infusion fluid to the inlet 20.

Thus, it is evident that there has been provided in accordance with the present invention a heat exchanger that may be used in a wearable fluid heater that fully satisfies the aims and objects, and achieves the advantages, hereinbefore set forth. As will be appreciated by those skilled in the art, although the present invention has been described in connection with illustrative embodiments and methods of use, many alternatives, modifications, and variations thereof are possible without departing from the present invention.

For example, although not shown in the Figures, each of the heating plates 136, 138 may include a plurality of grooves formed in the surfaces which contact the flexible walls 42, 40, respectively, directly above and below the fluid dividers in the heat exchanger 17. This increases the thermal resistances of the heat sinks 136, 138 in directions parallel to remaining planar portions of top and bottom surfaces, respectively, of the sinks 136, 138, and can increase the accuracy with which the processor 111 can control heating of the infusion fluid using the aforesaid techniques.

Other modifications are also possible. For example, rather than using the aforedescribed clamping valve mechanism for restricting fluid flow, the valve mechanism may instead comprise a pivoting lever (not shown) which is actuated by energization of a shape-memory wire attached to the lever to cut off fluid flow. Additionally, although the protection circuit 108 is shown in FIG. 7 as receiving the voltage signal output from the sensor 106, if heater 10 is appropriately modified, the circuit 108 may instead comprise its own thermistor-based temperature sensor.

In another modification, the processor 111 may be programmed to implement a diagnostic process upon being initially powered up, in which the processor 111 may cause the elements 120, 122 to maximally heat the fluid in the flow path 43 to a temperature above the predetermined maximum desired therefor, and thereafter, to determine whether the protection circuit 108 automatically deactivates the elements 120, 122 when the temperature at the outlet 92 exceeds that desired maximum. In this diagnostic mode, the processor 111 may be programmed also to determine if the length of time that it takes the heating elements 120, 122 to sufficiently heat the fluid in the flow path to cause the circuit 108 to deactivate the elements 120, 122 exceeds a maximum desired warm-up time.

Additionally, the processor 111 could alternatively be programmed to determine presence of inadequate flow rate through the flow path by determining whether the temperature difference between the input fluid temperature and the output fluid temperature does not fall within an empirically determined range expected for same, if the fluid flow rate were to exceed a desired level, at the power level supplied to the elements 120, 122.

Also, the processor 111 could be programmed to determine the actual flow rate in the flow path by determining the value of the "flow" variable as in the process of FIG. 12, and then using this value to determine therefrom the actual flow rate through the flow path based upon an empirical correlation programmed into the processor 111, which correlation is between experimentally measured flow rates through the flow path and respective values of the "flow" variable. The flow rate determined by the processor 111 to be present in the flow path may be indicated via LEDs (not shown) comprised in indicator/warming system 112, in a manner that is similar to that in which the fluid temperature is indicated via LEDs 51.

Figure 17:
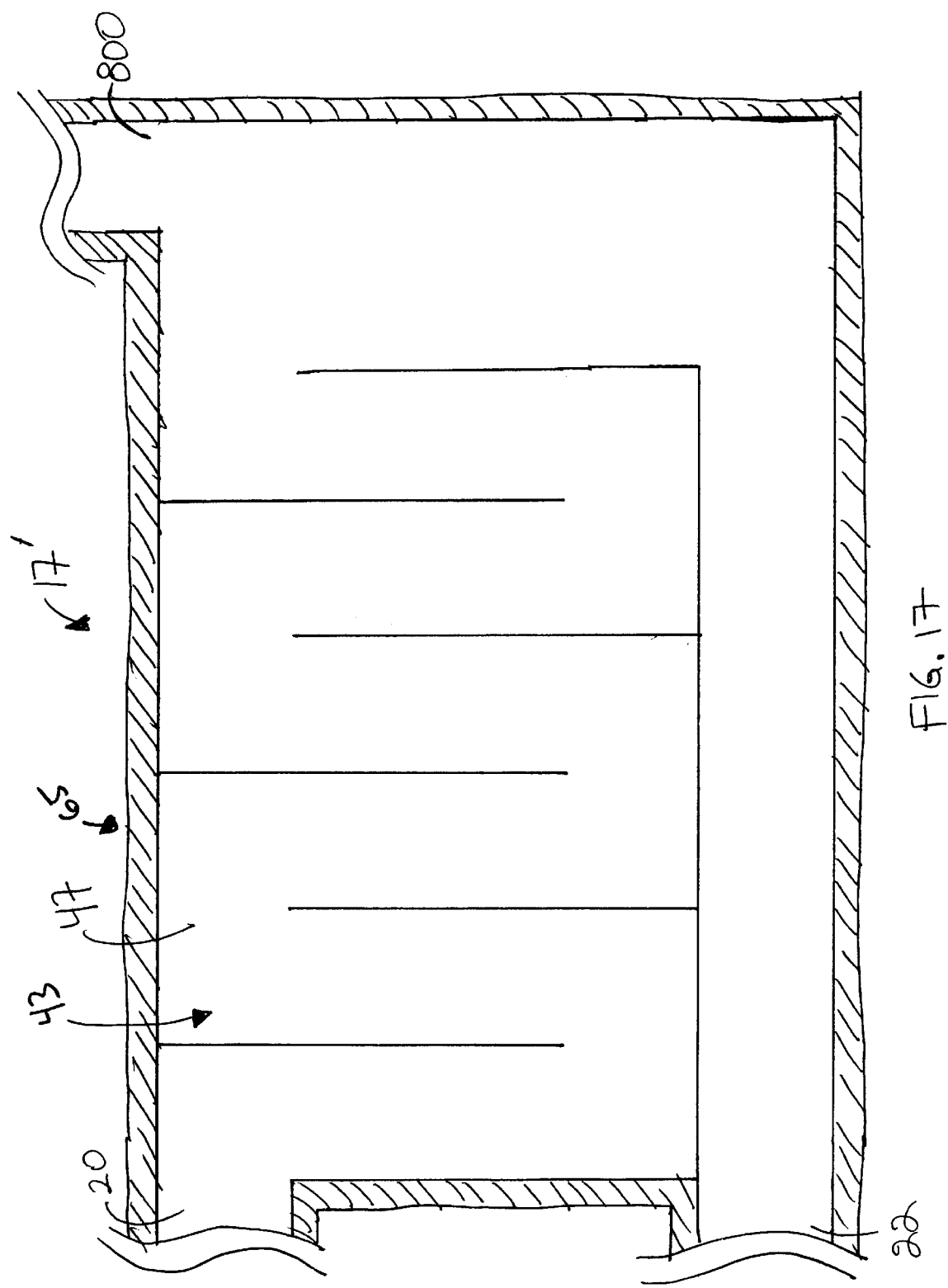
FIG. 17 is a schematic, longitudinal cross-sectional view of another embodiment of the heat exchanger of the present invention.

Yet other modifications are also possible. For example, FIG. 17 illustrates the construction of another embodiment 17' of a heat exchanger according to the present invention. Unless stated specifically to the contrary herein, it should be understood that the construction and operation of the heat exchanger 17' may be the same as those of heat exchanger 17.

As shown in FIG. 17, heat exchanger 17– includes a member 65 that includes an infusion fluid inlet 20 and two infusion fluid outlets 22, 800. Although not shown in FIG. 17, it should be understood that, in use, the heat exchanger 17– also includes two flexible sheets 40, 42. Infusion fluid flow path 43 through the heat exchanger 17' is defined by the flexible sheets 40, 42 together with the member 65, and fluid inlet 20, outlets 22, 800, and serpentine channel 47 between the inlet 20 and outlets 22, 800.

In this embodiment, the inlet 20 comprises a female luer fitting (not shown) for being mated to a corresponding male luer fitting (not shown) whereby to permit the heat exchanger 17' to receive, via tubing 804 (see FIG. 22), an unheated flow of infusion fluid from an external gravity-feed infusion fluid source 810; the outlet 22 comprises a male luer fitting (not shown) for being mated to a corresponding female luer fitting (not shown) whereby to permit transmission, via tubing (e.g., tubing 604 in FIG. 15) connected to the corresponding female fitting, of the heated infusion fluid from the heat exchanger 17' to the infusion situs 606 of patient 608.

Outlet 800 of the heat exchanger 17' may also comprise a respective male luer fitting (not shown) for being mated to a corresponding female luer fitting (not shown) comprised in tubing 802 so as to permit fluid communication between the outlet 800 and tubing 802. Tubing 802 connects the outlet 800 to the fluid source 810 via a wye 812. Wye 812 is positioned upstream of the inlet 20 relative to the outlet 813 of the source 813, and permits fluidic communication among the tubing 804, outlet 813, and the tubing 802.

Tubing 802 comprises a conventional check valve 806 that is positioned upstream of the wye 812. Valve 806 is constructed to permit flow of fluid out of the heat exchanger 17' to the wye 812 via the outlet 800 and the tubing 802, and to prevent fluid from flowing from the source 810 into the exchanger 17' via the tubing 802 and outlet 800.

With the exception of check valve 806 and portion 808, tubing 802 may be made of air and liquid tight plastic. Portion 808, however, is a porous hydrophobic membrane 808 that is positioned upstream of the wye 812 but downstream of the valve 806. Membrane 808 may be made of Gortex™ expanded polytetrafluoro-ethylene. The size of the pores in membrane 808 may be approximately 0.45 micron in diameter, although, as will be appreciated by those skilled in the art, the pores in membrane 808 may be differently sized without departing from this embodiment of the present invention. The size of the pores in membrane 808 and the position of the membrane 808 in the tubing 802 are selected so as to permit entrained gas bubbles in fluid flowing through the tubing 802 to pass out of the tubing 802 through the membrane 808 into the ambient environment, while preventing the fluid and bacteria (and/or other contaminants) from passing through the membrane 808. Such gas bubbles may result from, e.g., precipitation of dissolved air out of the infusion fluid during heating of the fluid in the heat exchanger 17'.

When heat exchanger 17' is used in heater 10, heater 10 may comprise a heat exchanger pressurizing and gas purging mechanism 900. Mechanism 900 may include eight separate, identical cam mechanisms. Inasmuch as each of the cam mechanisms comprised in mechanism 900 has an identical construction, the construction of only one such cam mechanism 902 (illustrated in FIG. 18) will be described herein.

Figure 18:
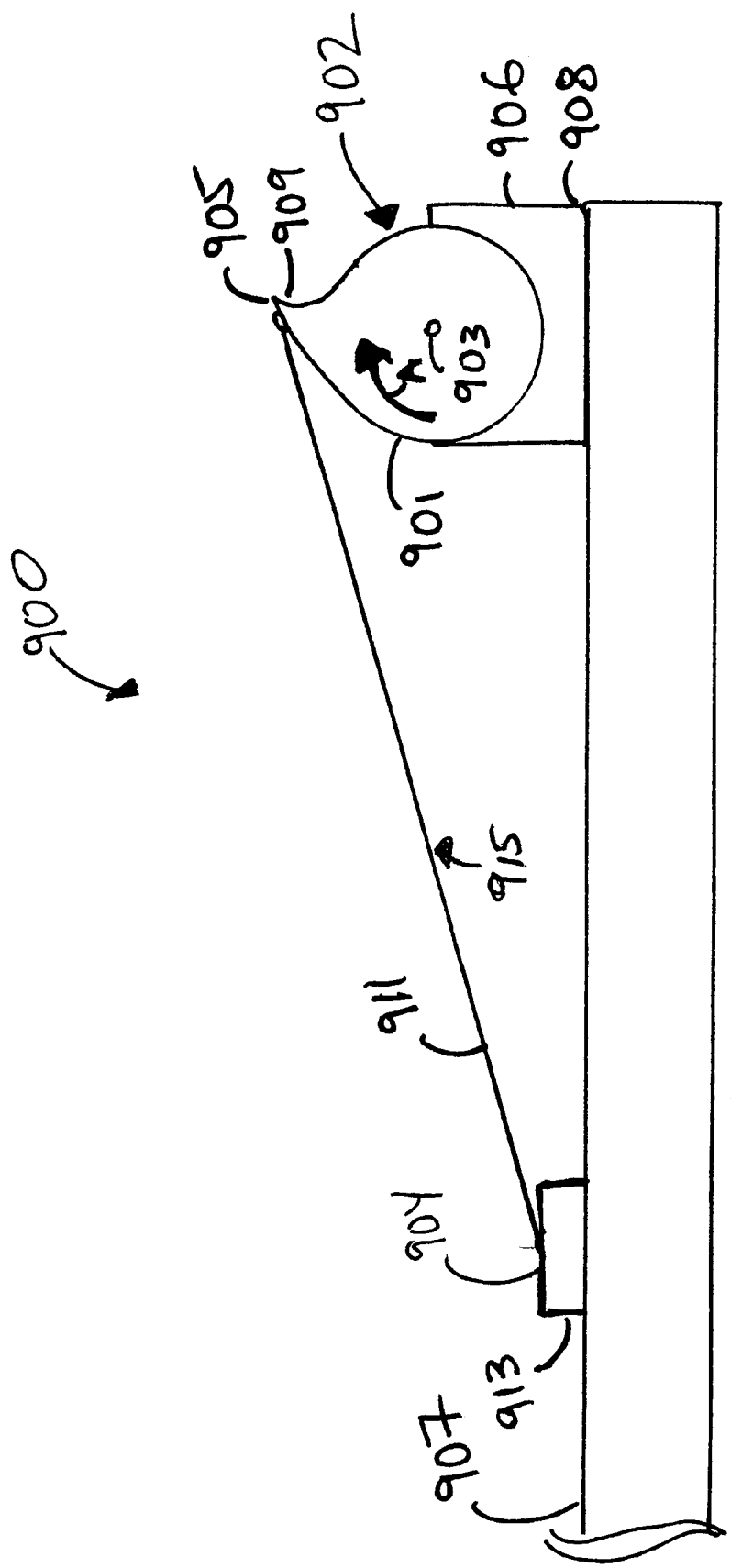
FIG. 18 is a highly schematic diagram illustrating one pressurizing cam mechanism that may be used to apply pressure force to the embodiment of the heat exchanger shown in FIG. 17.
Figure 19:
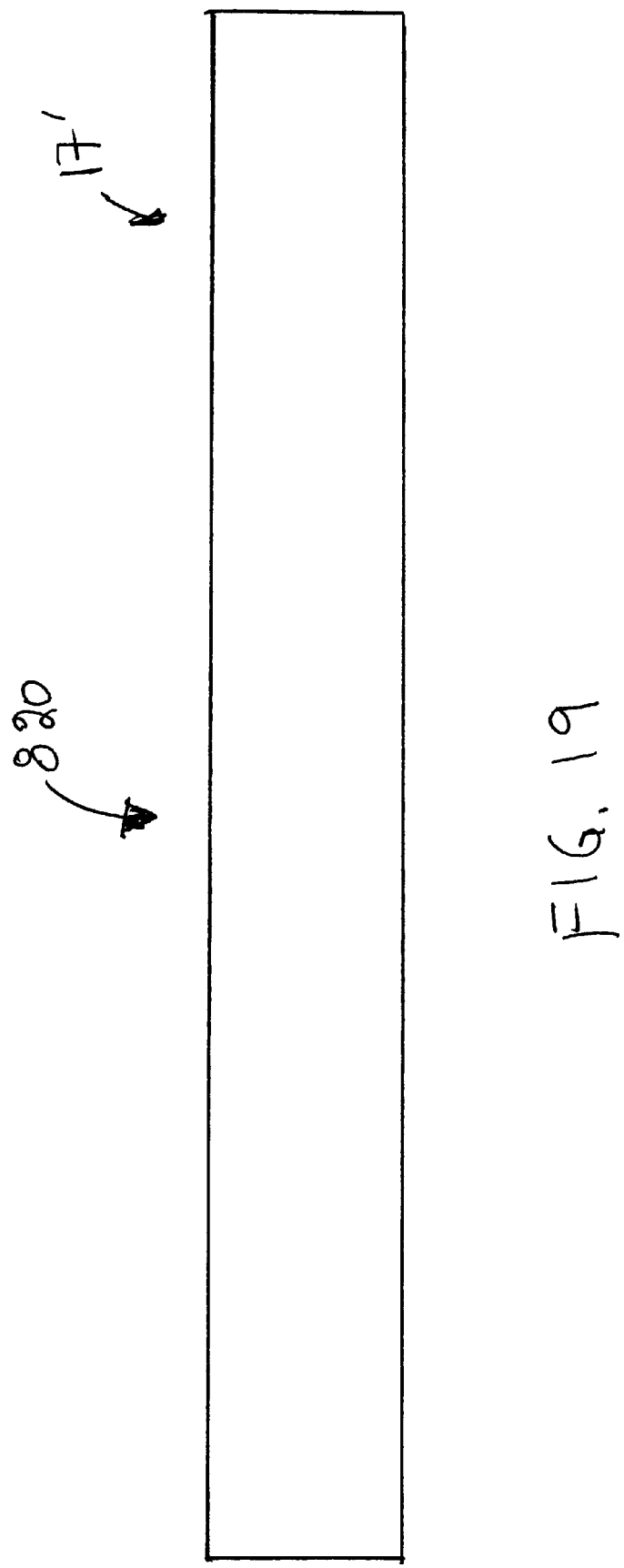
FIGS. 19–21 are schematic, transverse cross-sectional views of the heat exchanger of FIG. 17 for facilitating illustration of operation of the heat exchanger of FIG. 17.
Figure 20:
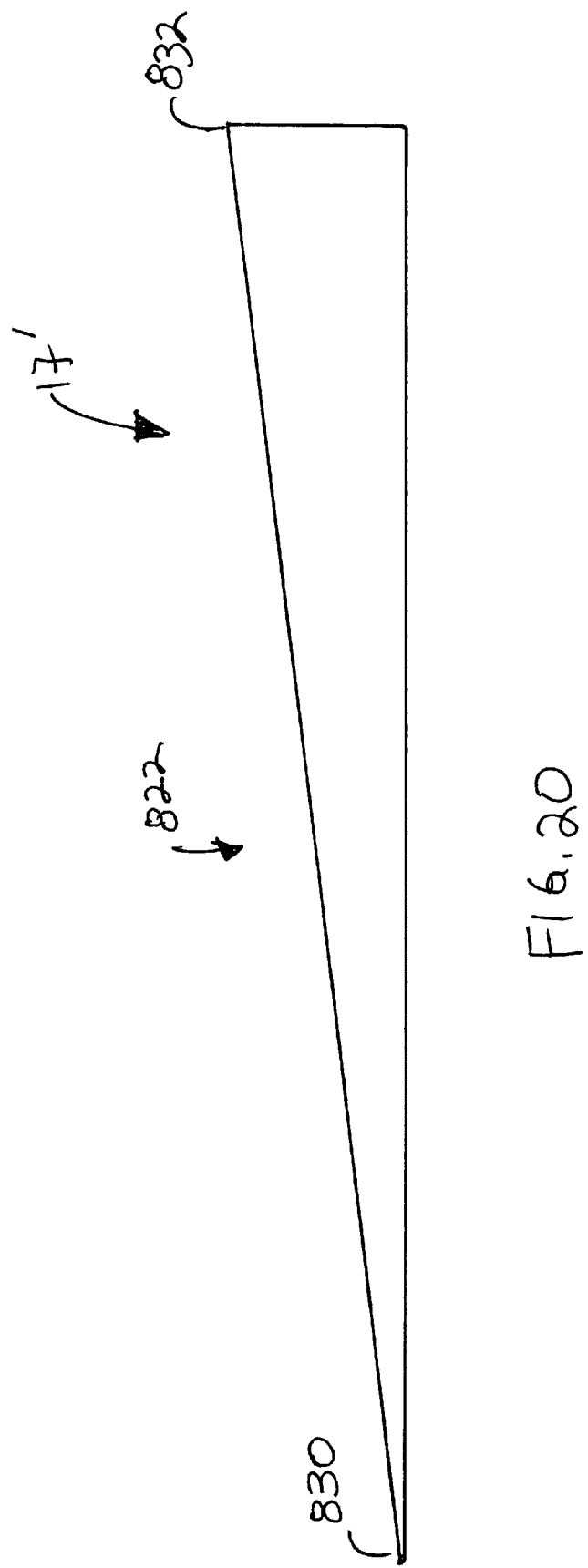
Figure 21:
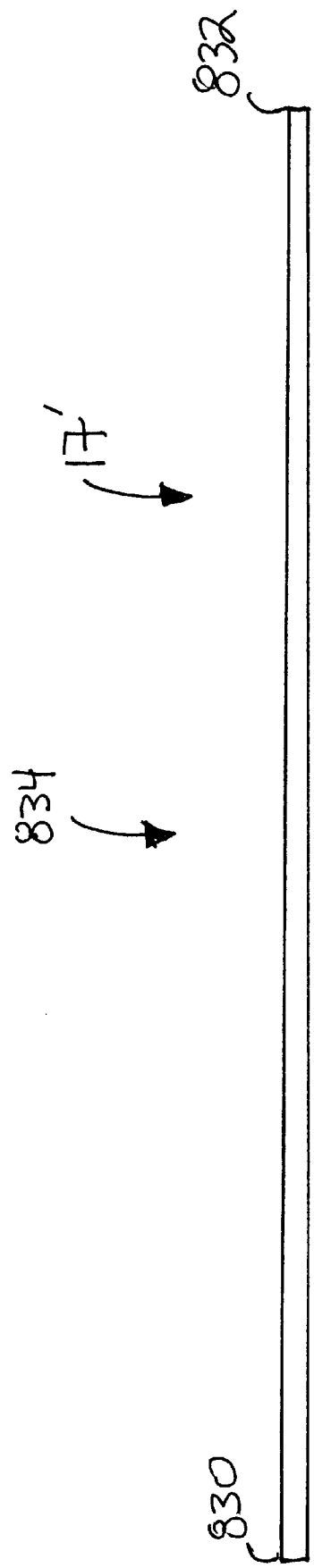

As shown in FIG. 18, each cam mechanism 902 includes a respective tear-drop-shaped cam 901 that is rotationally-mounted to a respective shaft 903. Each cam 901 includes a pointed end portion 909 whose radius from the center of the cam 901 is significantly greater than that of the remainder of the cam 901. Each such shaft 903 is mounted to a respective support 906. Each of these supports is attached to a respective corner (e.g., corner 908 in the case of support 906) of either the top surface 907 of the panel 155 or the bottom surface 916 of panel 157; thus, each of the eight cam mechanisms comprised in the mechanism 900 is positioned adjacent a respective corner 908, 910, 912, or 914 of the top surface 907 of the panel 155 or a respective corner 918, 920, 922, or 924 of the bottom surface 916 of the panel 157, with only a single respective cam mechanism being positioned in a single respective such corner.

Each respective cam mechanism 902 also includes a respective shape-memory alloy actuating element 915. Element 915 comprises a shape-memory alloy e.g., (a nitinol-type) wire or filament 911 having two opposite ends 904, 905. One end 904 of the wire is physically attached to a support 913, and the other end 905 of the wire 911 is physically attached to the pointed-end 909 of the tear-drop-shaped cam 901. Although not shown in the Figures, the end 904 of the wire 911 is also electrically connected to the power supply 116 via a respective controllable switch whose state is controlled by the processor 111. When electric power is supplied to the wire 911, the wire 911 heats up to its shape-change transition temperature, and changes shape and/or length so as to cause the cam 901 to rotate about shaft 903 in the direction indicated by the arrow A in FIG. 18. Conversely, after the power is cut off from the wire 911, the wire 911 cools to below its transition temperature and returns to its initial, relaxed shape and/or length; this causes the cam 901 to rotate about shaft 903 in a direction that is opposite to that indicated by arrow A. It is important to note that in FIG. 18, the cam mechanism 902 is shown in a state wherein electrical power is being supplied to the wire 911 and the wire 911 has already changed shape and/or length so as to cause the cam 901 to rotate in the direction A to maximum possible extent.

The manner in which gas is purged from the fluid in the heater exchanger 17' using the mechanism 900 will now be described with reference being made to FIG. 17–23. In operation, when the heat exchanger 17' is used in the heater 10, the exchanger 17' is held in the heater 10 by the housing 12 such that inlet 20 and outlet 22 of the exchanger 17' extend from the same side of the heater 10. As the heater 10 heats the infusion fluid flowing through the flow path 43 in the heat exchanger 17', the processor 111 may determine the amount of thermal energy imparted to the fluid (based upon the flow variable, in the manner described previously), and may compare the thermal energy imparted to a predetermined thermal energy value that has been empirically determined to be the thermal energy at which the maximum amount of precipitated gas may be removed from the fluid without unduly interfering with the supplying of infusion fluid to the patient or being detrimental to the patient's health. When the processor 111 determines that this predetermined amount of thermal energy has been imparted to the fluid in the heat exchanger 17', or alternatively, that gas is present in the flow path 43 of exchanger 17' (using the aforedescribed techniques for same), the processor 111 may cause electrical power to be supplied to the shape-memory alloy wires comprised in the four respective cam mechanisms closest to the inlet 20 and outlet 22 of the heat exchanger 17' (e.g., the two cam mechanisms positioned at the corners 910, 912, respectively, of the panel 155, and the two cam mechanisms positioned at the corners 920, 922, respectively, of the panel 157). The shape-memory alloy wires and cams comprised in these four cam mechanisms are dimensioned and configured such that, when electrical power is supplied to these wires, the wires change shape and/or length so as to cause the respective cams to which they are attached to rotate such that the respective tear-drop pointed-ends of the respective cams impinge upon the housing 12, and thereby, cause a first force to be applied to the heat exchanger 17'. The application of the first force to the heat exchanger 17' collapses the end 830 of the heat exchanger 17' that is closest to these four cam mechanisms, occludes the inlet 20 and outlet 22 of the heat exchanger 17', and causes the transverse cross-sectional shape of the heat exchanger 17' to change from its initial generally rectangular shape 820 to the generally triangular shape 822 shown in FIG. 20. This prevents flow of fluid into the inlet 20 and out of the outlet 22.

Thereafter, the processor 111 may cause electrical power to be supplied to the respective shape-memory alloy wires of the remaining four cam mechanisms comprised in mechanism 900. The shape-memory alloy wires and cams comprised in these remaining four cam mechanisms are dimensioned and configured such that, when electrical power is supplied to these wires, the wires change shape and/or length so as to cause the respective cams to which they are attached to rotate such that the respective tear-drop pointed-ends of the respective cams impinge upon the housing 12, and thereby, cause a second force to be applied to the heat exchanger 17'. The application of the second force to the heat exchanger 17' causes the end 832 of the heat exchanger 17' that is closest to these four remaining cam mechanisms to collapse, and forces the fluid (and any entrained gas therein) present in the heat exchanger 17' out of the heat exchanger 17' via the outlet 800. After both the first and second forces have been applied to the heat exchanger 17, the transverse cross-section of the heat exchanger 17' has the shape 834 shown in FIG. 21.

When the first and second forces are applied to the heat exchanger 17', the fluid forced out of the heat exchanger 17' via outlet 800 enters tubing 802, and thence passes through check valve 806. After passing through the valve 806, the fluid encounters the membrane portion 808, and gas entrained in the fluid is vented through the membrane portion 808 to the ambient environment. Thereafter, the fluid reaches wye 812, and may be recirculated to the heat exchanger 17', via tubing 804 and inlet 20, after the first and second forces are no longer applied to the heat exchanger 17'.

The processor 111 may be programmed to stop electrical power from being supplied to the wires of the cam mechanisms after an empirically determined amount of time has elapsed after application of the first and second forces to the heat exchanger 17' that is sufficient to permit all of the fluid and any entrained air in the heat exchanger 17' to be flushed out from the heat exchanger 17' via outlet 800. Once electrical power has ceased being supplied to the wires of the cam mechanisms, the wires change shape and/or length so as to cause the cams comprised in the cam mechanisms to rotate such that the cams no longer impinge upon the housing 12, thereby causing application of the first and second forces to the heat exchanger 17' to cease. This causes the transverse cross-sectional shape of the heat exchanger 17' to change from the shape 834 shown in FIG. 21 to the shape 820 shown in FIG. 19.

Advantageously, by utilizing the heat exchanger 17' and gas purging mechanism shown in FIGS. 17–22, the gas present in the fluid in the exchanger 17' may be removed from the infusion fluid prior to being infused into the patient, regardless of the orientation of the heater 10, while maintaining the sterility of the fluid and permitting the fluid from which gas has been purged to be later infused into the patient.

Figure 22:
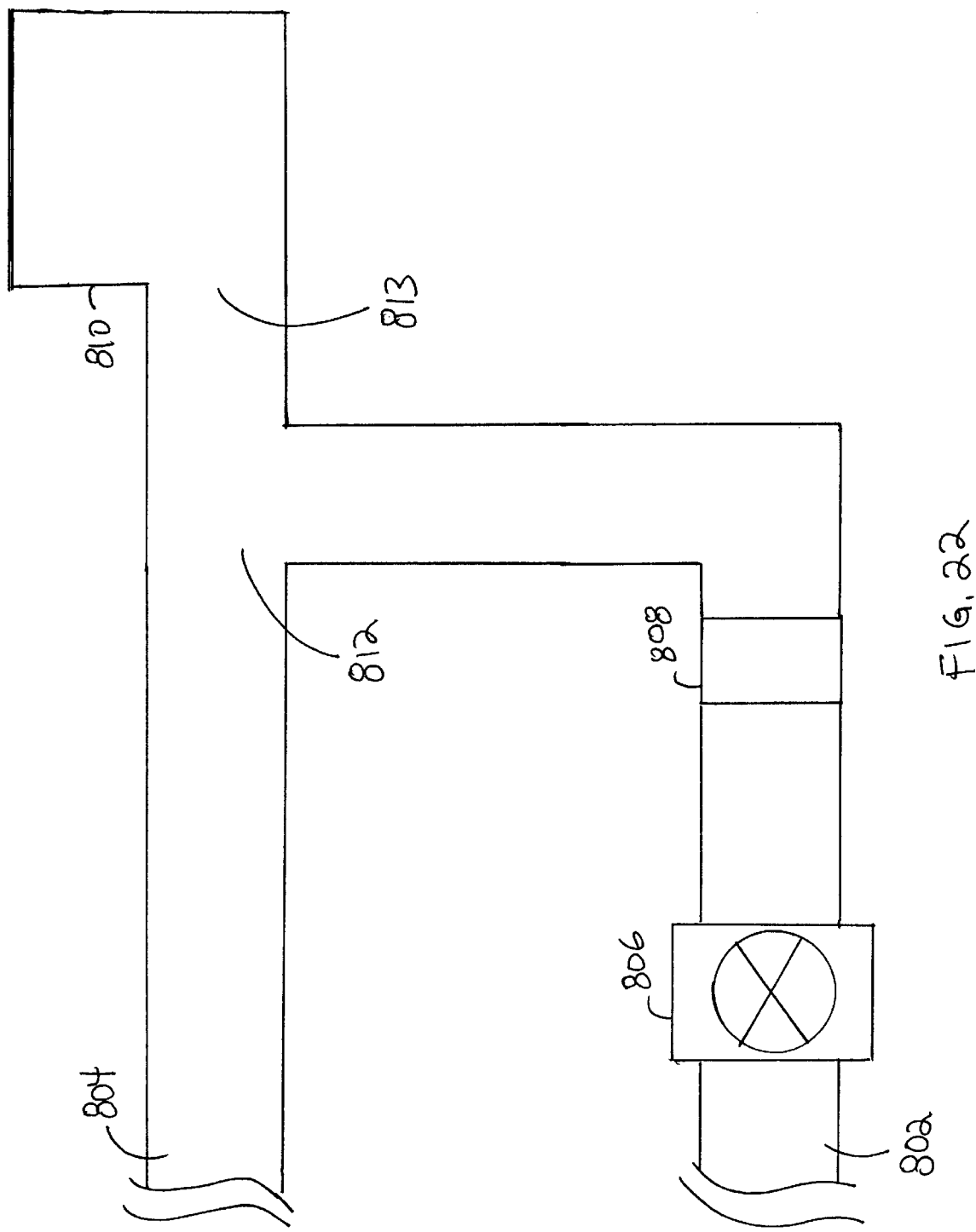
FIGS. 22 and 23 are schematic diagrams illustrating infusion fluid delivery and gas purging systems that may be used with the heat exchanger of FIG. 17.
Figure 23:
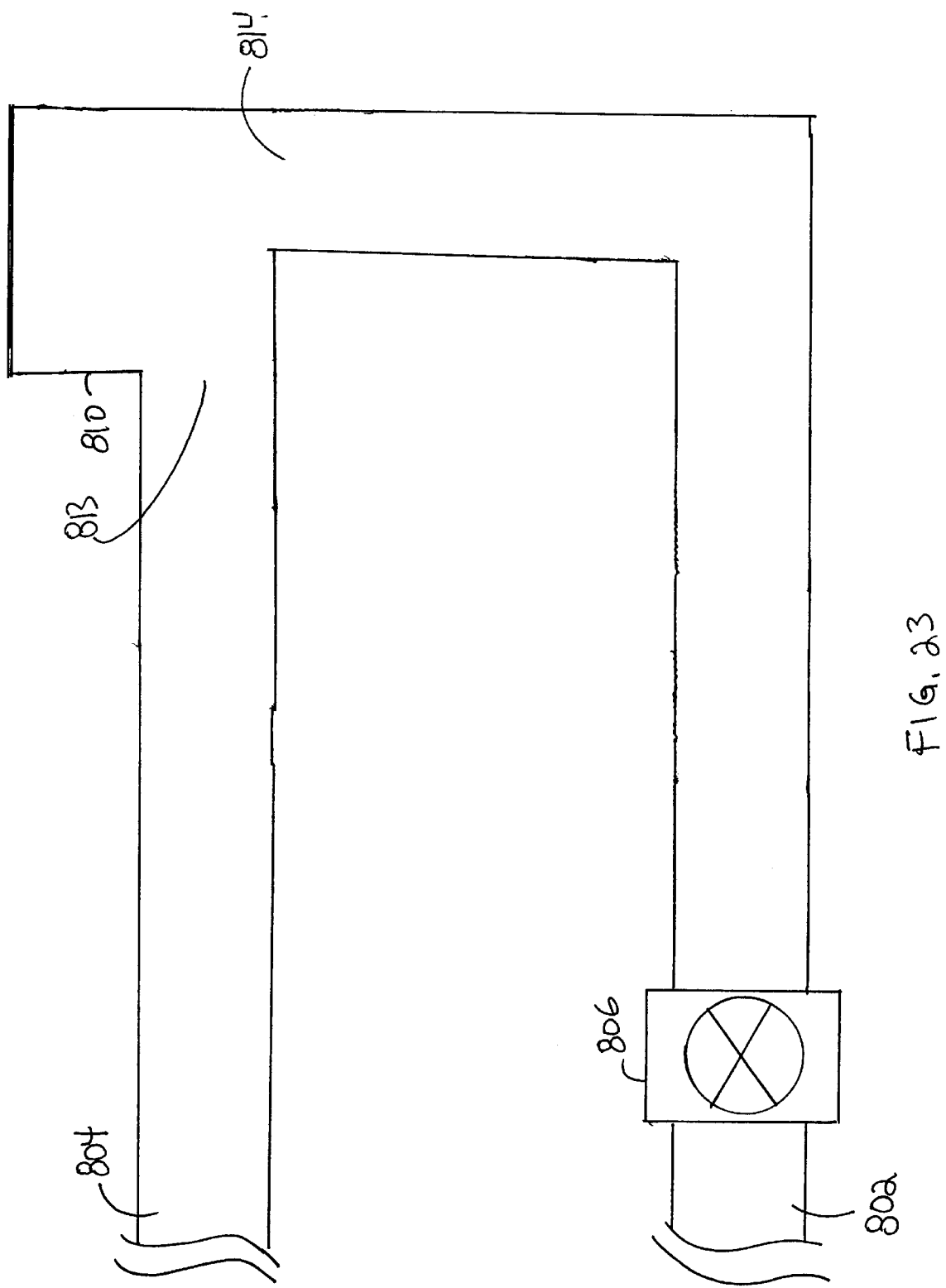

Further modifications are also possible. For example, as shown in FIG. 23, the tubing 802, 804 may be modified so as to eliminate wye 812. In the alternate arrangement illustrated in FIG. 23, tubing 802 is in fluid communication with an inlet 814 of the source 810, and tubing 804 is in fluid communication with an outlet 813 of the source 810. Also in this alternate arrangement, the membrane 808 illustrated in FIG. 22 is eliminated, and the tubing 802 provides a return path for fluid in the heat exchanger 17' and gas entrained in the fluid to be recirculated to the source 810 from the heat exchanger 17' when the pressurizing action of the mechanism 900 is actuated; once the fluid has been recirculated to the source 810, the entrained gas may be naturally separated and removed from the fluid in the source 810 as a result of gravity and the relative differences in density between fluid and the entrained gas, and the fluid from which the gas has been separated and removed may be resupplied to the heat exchanger 17' for infusion into the patient.

Figure 25:
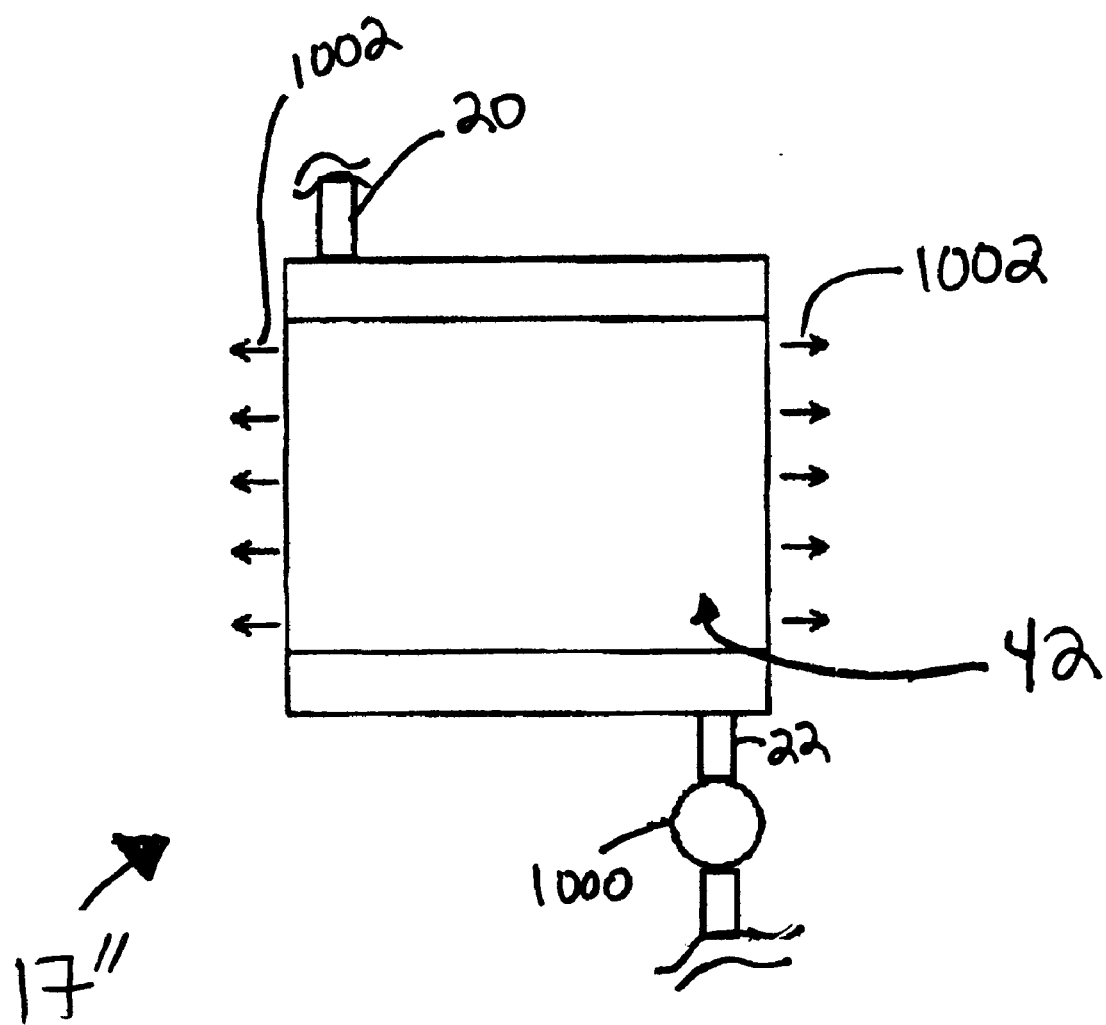
FIGS. 25–26 are highly schematic diagrams illustrating features of another embodiment of the present invention.
Figure 26:
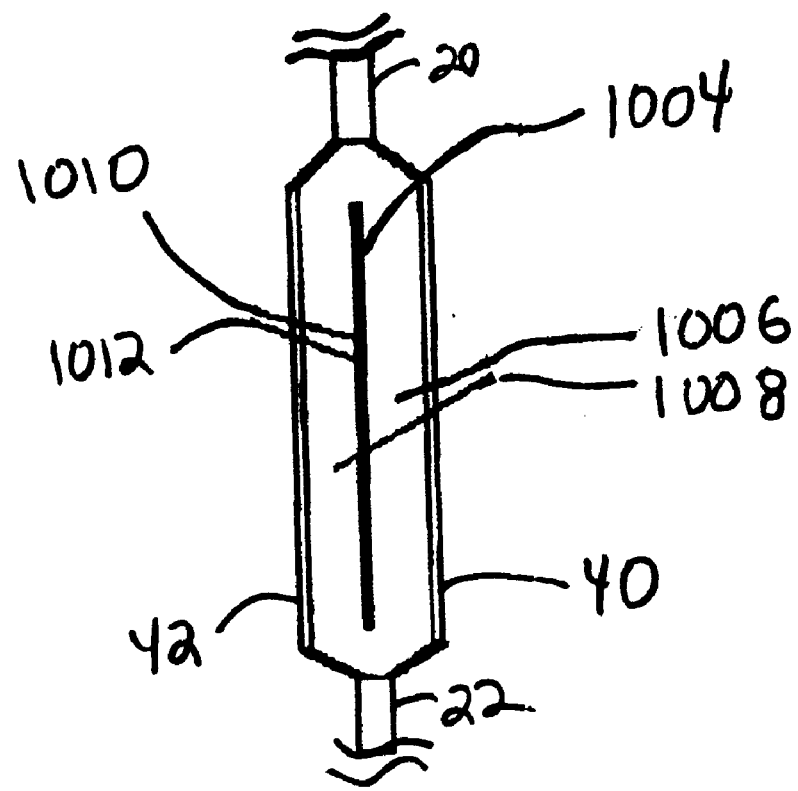

Additional modifications are also possible. For example, a variation 17" of the heat exchanger 1001 is illustrated in FIGS. 25 and 26. FIG. 25 is an outside schematic illustration of the exchanger 17"; FIG. 26 is a longitudinal cross-sectional schematic illustration of the exchanger 17". Unless stated specifically to the contrary herein, it should be understood that the construction and operation of the embodiment 17" are substantially identical to the construction and operation of the embodiment 1001.

In embodiment 17", two serpentine flowpaths (not explicitly shown in FIGS. 25–26 for purposes of clarity of illustration) identical in construction to flowpath 43 are placed in respective channels 1006, 1008. The flowpath in channel 1006 is sandwiched between and defined by an outer non-porous membrane 40 and an inner porous, hydrophobic membrane 1010. The flowpath in channel 1008 is sandwiched between and defined by an outer non-porous membrane 42 and an inner porous, hydrophobic membrane 1012. Both of the flowpaths in the channels 1006, 1008 are in fluid communication with a common fluid inlet 20 to the exchanger 17". Both of the flowpaths in the channels 1006, 1008 are also in fluid communication with a common fluid outlet 22 to the exchanger 17".

A relatively small gap 1004 exists between the porous membranes 1010, 1012. Gap 1004 is dimensioned so to permit venting of gas (in the manner referenced by numeral 1002 in FIG. 25) through the porous membranes 1010, 1012 from the fluid flowing in the two flowpaths in exchanger 17". Advantageously, by constructing the exchanger 17" in this manner, the ability to transfer heat (i.e., through the non-porous membranes 40, 42) into the fluid flowing through the exchanger 17" is improved compared to that which is possible using heat exchanger 1001.

Yet further modifications are also possible. Accordingly, the present invention is intended to be viewed quite broadly as being limited only as set forth in the hereinafter appended claims.

What is claimed is:

1. A heat exchanger useable in a fluid heater, the heat exchanger comprising:
    two flexible walls, at least one of the walls for contacting a respective heating element of the heater when the heat exchanger is used in the heater, wherein one of the flexible walls is relatively thin polycarbonate sheet and the other flexible wall is a relatively thick microporous hydrophobic membrane; and
    a flow path through the heater, defined at least in part by the at least one of the flexible walls, when the heat exchanger is used in the heater;
    wherein the heat exchanger, when used in the heater, is physically unattached to the heater and is removable from the heater.

2. A heat exchanger according to claim 1, wherein the microporous membrane comprises expanded polytetrafluoroethylene.

3. A heat exchanger useable in a fluid heater, the heat exchanger comprising:
    two flexible walls, at least one of the walls for contacting a respective heating element of the heater when the heat exchanger is used in the heater;
    a flow path through the heater, defined at least in part by at least one of the flexible walls when the heat exchanger is used in the heater, wherein the flow path includes a fluid inlet, a fluid outlet, and a serpentine channel between the inlet and outlet; and
    another fluid outlet, and being constructed such that when the heat exchanger is impinged upon by a pressurizing mechanism, the inlet and one of the outlets become occluded, and fluid and gas in the flow path may be forced by pressure forces applied to the heat exchanger by the pressurizing mechanism through the another outlet and out of the heat exchanger,
    wherein the heat exchanger, when used in the heater, is physically unattached to the heater and is removable from the heater.

4. A heat exchanger according to claim 3, wherein the mechanism comprises a cam system that applies a first force and a second force to the heat exchanger, the first force causing an occluding of the inlet and the one outlet, the second force causing the fluid and the gas to be forced out of the heat exchanger.

5. A heat exchanger according to claim 3, further comprising a hydrophobic membrane that vents the gas to an ambient environment.

6. A heat exchanger according to claim 5, wherein the membrane is in fluid communication with the inlet.

7. A heat exchanger according to claim 6, further comprising a check valve for preventing return fluid flow into the heat exchanger via the another outlet.

8. A heat exchanger according to claim 3, wherein the mechanism comprises a cam that may be actuated to apply pressure to the heat exchanger.

9. A heat exchanger according to claim 8, wherein a wire actuates the cam.

10. A heat exchanger according to claim 9, wherein the wire is heated by application of electricity to the wire.

11. A heat exchanger according to claim 9, wherein, in use, the heat exchanger is disposed in a housing, and the cam is positioned between the housing and the heat exchanger.

12. A heat exchanger useable in a fluid heater, the heat exchanger comprising:
    two flexible walls, at least one of the walls for contacting a respective heating element of the heater when the heat exchanger is used in the heater;
    a flow path through the heater, defined at least in part by the at least one of the flexible walls, when the heat exchanger is used in the heater; and
    further comprising two fluid outlets and a fluid inlet, and a check valve that prevents a fluid flow into the heat exchanger via one of the outlets.

13. A heat exchanger according to claim 12, wherein the exchanger is for use with a hydrophobic membrane for venting gas from the fluid.

14. A heat exchanger useable in a fluid heater, the heat exchanger comprising:
    two flexible walls, at least one of the walls for contacting a respective heating element of the heater when the heat exchanger is used in the heater; wherein one of the flexible walls is porous, and
    a flow path through the heater, defined at least in part by the at least one of the flexible walls, when the heat exchanger is used in the heater;
    a pressure regulating valve for use in preventing ambient air from flowing into the heat exchanger,
    wherein the heat exchanger, when used in the heater, is physically unattached to the heater and is removable from the heater.

15. A heat exchanger according to claim 14, wherein the flow path includes a fluid inlet, a fluid outlet, and a serpentine channel between the inlet and outlet.

16. A heat exchanger according to claim 14, wherein the heater and heat exchanger are dimensioned to be wearable by a patient adjacent a fluid infusion situs of the patient.

17. A heat exchanger according to claim 14, wherein the heat exchanger is constructed such that, when in use in the heater, the heat exchanger is held in place by the heater against the heating elements.

18. A heat exchanger according to claim 14, wherein the at least one of the flexible walls that is porous is also hydrophobic.

19. A heat exchanger according to claim 14, wherein at least one of the flexible walls includes a plurality of pores that are dimensioned to vent gas.

20. A heat exchanger according to claim 19, wherein the pores are also dimensioned so as to prevent flow of fluid through the pores.

21. A heat exchanger according to claim 20, wherein the pores are also dimensioned so as to prevent bacteria from passing through the pores.

22. A heat exchanger according to claim 14, wherein one of the flexible walls is a relatively thin polycarbonate sheet and the other flexible wall is a relatively thick microporous hydrophobic membrane.

23. A heat exchanger according to claim 22, wherein the microporous membrane comprises expanded polytetrafluroethylene.

24. A heat exchanger according to claim 14, further comprising another fluid outlet, and being constructed such that when the heat exchanger is impinged upon by a pressurizing mechanism, the inlet and one of the outlets become occluded, and fluid and gas in the flow path may be forced by pressure forces applied to the heat exchanger by the mechanism through the another outlet and out of the heat exchanger.

25. A heat exchanger according to claim 24, wherein the mechanism comprises a cam system that applies a first force and a second force to the heat exchanger, the first force causing an occluding of the inlet and the one outlet, the second force causing the fluid and the gas to be forced out of the heat exchanger.

26. A heat exchanger according to claim 24, further comprising a hydrophobic membrane that vents the gas to an ambient environment.

27. A heat exchanger according to claim 24, wherein the mechanism comprises a cam that may be actuated to apply pressure to the heat exchanger.

* * * * *